United States Patent [19]
Partis et al.

[11] Patent Number: 5,411,970
[45] Date of Patent: May 2, 1995

[54] METHOD OF INHIBITING LENTIVIRUS

[75] Inventors: Richard A. Partis, Evanston; Francis J. Koszyk, Prospect Heights; Richard A. Mueller, Glencoe, all of Ill.

[73] Assignee: G. D. Searle & Co., Skokie, Ill.

[21] Appl. No.: 170,593

[22] Filed: Dec. 21, 1993

Related U.S. Application Data

[60] Division of Ser. No. 929,325, Aug. 13, 1992, Pat. No. 5,310,745, which is a continuation-in-part of Ser. No. 639,472, Jan. 10, 1991, abandoned, which is a continuation-in-part of Ser. No. 418,091, Oct. 12, 1989, Pat. No. 5,003,072, which is a continuation-in-part of Ser. No. 266,767, Nov. 3, 1988, abandoned.

[51] Int. Cl.$^6$ ............................................. A61K 31/445
[52] U.S. Cl. ..................................... 514/315; 514/328
[58] Field of Search .................................. 514/328, 315

[56] References Cited

U.S. PATENT DOCUMENTS

| | | | |
|---|---|---|---|
| 4,182,767 | 1/1980 | Murai et al. | 546/242 X |
| 4,348,402 | 9/1982 | Kinast et al. | 424/267 |
| 4,639,436 | 1/1987 | Junge et al. | 514/24 |
| 4,849,430 | 7/1989 | Fleet et al. | 514/315 |
| 5,003,072 | 3/1991 | Partis et al. | 546/243 |

FOREIGN PATENT DOCUMENTS 8703903 7/1987 WIPO.

OTHER PUBLICATIONS

Frank et al., Antimicrob. Agents Chemother. 31, 1369–1374 (1978).
Sunkara et al., Soc. Complex Carbohyd. 17th Ann. Meet., San Antonio, Nov. 3–5, 1988, Abst. 9.
Chem. Abst. 86, 167851r (1987).
Chem. Abst. 68, 78526Z (1968).
Chem. Abst. 67, 3207s (1967).
Chem. Abst. 92, 7688m (1980).
Chem. Abst. 84, 44569F (1976).

*Primary Examiner*—Richard L. Raymond
*Assistant Examiner*—Mary C. Cebulak
*Attorney, Agent, or Firm*—Scott J. Meyer

[57] ABSTRACT

A method of inhibiting lentivirus is disclosed which comprises mammalian host susceptible to said lentivirus with a virally inhibitory effective amount of an O-acylated derivative of 1,5-dideoxy-1,5-imino-D-glucitol and their N-alkyl, N-acyl and N-aroyl derivatives in which from one to four of the free hydroxyl groups are O-acylated with carboxylic alkanoyl radicals selected from the group consisting of $\omega,\omega,\omega$-trifluoroalkanoyl having from three to eight carbon atoms, carboxylic cycloalkanoyl groups having from four to eight carbon atoms and carboxylic acyclic alkanoyl groups having from two to ten carbon atoms, wherein the N-aroyl groups contain from 7 to 14 carbon atoms, the N-acyl groups contain from 4 to 8 carbon atoms and the N-alkyl groups contain from 1 to 14 carbon atoms.

3 Claims, No Drawings

METHOD OF INHIBITING LENTIVIRUS

CROSS-REFERENCE TO RELATED APPLICATION

This is a division of application Ser. No. 07/929,325, filed Aug. 13, 1992, now U.S. Pat. No. 5,310,745 which is a continuation-in-part of application Ser. No. 07/639,472, filed Jan. 10, 1991, now abandoned, which is a continuation-in-part of application Ser. No. 07/418,091, filed Oct. 12, 1989, now U.S. Pat. No. 5,003,072, which in turn is a continuation-in-part of application Ser. No. 07/266,767, filed Nov. 3, 1988, now abandoned.

BACKGROUND OF THE INVENTION

This invention relates to novel antiviral compounds and, more particularly, to O-acylated derivatives of 1,5-dideoxy-1,5-imino-D-glucitol and their N-alkyl, N-acyl and N-aroyl derivatives. These compounds are inhibitors of visna virus, a pathogenic virus for sheep and goats. These antiviral compounds also have potential use for the treatement of acquired immune deficiency syndrome (AIDS) and AIDS-related complex (ARC).

Acquired immune deficiency syndrome, which only a few years ago was a medical curiosity, is now a serious disease. As a consequence, a great effort is being made to develop drugs and vaccines to combat AIDS. The AIDS virus, first identified in 1983, has been described by several names. It is the third known T-lymphocyte virus (HTLV-III) and has the capacity to replicate within cells of the immune system and thereby lead to a profound destruction of T4+ T-cells (or CD4+ cells). See, e.g., Gallo et al., Science 224, 500–503 (1984), and Popovic et al., Ibid., 497–500 (1984). This retrovirus has been known as lymphadenopathy-associated virus (LAV) or AIDS-related virus (ARV) and, most recently, as human immunodeficiency virus (HIV). Two distinct AIDS viruses, HIV-1 and HIV-2, have been described. HIV-1 is the virus originally identified in 1983 by Montagnier and co-workers at the Pasteur Institute in Paris [Ann. Virol. Inst. Pasteur 135 E, 119–134 (1984)], while HIV-2 was more recently isolated by Montagnier and his coworkers in 1986 [Nature 326, 662–669 (1987)]. As used herein, HIV is meant to refer to these viruses in a generic sense.

Although the molecular biology of AIDS is beginning to be unraveled and defined, much more needs to be learned and understood about this disease. In the meantime, numerous approaches are being investigated in the search for potential anti-AIDS drugs and vaccines. Development of an AIDS vaccine is hampered by lack of understanding of mechanisms of protective immunity against HIV, the magnitude of genetic variation of the virus, and the lack of effective animal models for HIV infection. See, for example, Koff and Hoth, Science 241, 426–432 (1988).

The first drug to be approved by the U.S. Food and Drug Administration (FDA) for treatment of AIDS was zidovudine, better known under its former name, azidothymidine (AZT). Chemically, this drug is 3'-azido-3'-deoxythymidine. This drug was originally selected as a potential weapon against AIDS because it was shown to inhibit replication of the virus in vitro. Such in vitro tests are useful and virtually the only practical method of initially screening and testing potential anti-AIDS drugs. A serious drawback of AZT, however, is its toxic side-effects. Thus, the search for better anti-AIDS drugs continues.

The HIV inhibitory activity of 1,5-dideoxy-1,5-imino-D-glucitol (deoxynojirimycin) and its N-methyl derivative is disclosed in PCT Inter. Appln. 87/03903, published Jul. 2, 1987. The substantially more effective anti-HIV activity of the N-butyl derivative of deoxynojirimycin is disclosed in U.S. Pat. No. 4,849,430. Other N-substituted derivatives of deoxynojirimycin having anti-HIV activity are described in EP Applns. 344,383 and 345,104, published Dec. 6, 1989, and EP Appln. 350,012, published Jan. 10, 1990.

U.S. Pat. Nos. 4,182,767 and 4,639,436 show the syntheses and antihyperglycemic use of N-alkyl derivatives of deoxynojirimycin. These patents suggest the use of acyl blocking groups or hydroxyl-protective groups in the syntheses of the desired antihyperglycemic products. However, these blocking groups are proposed only for the preparation of the intermediates and are removed with no isolation or characterization of compounds for antiviral use.

BRIEF DESCRIPTION OF THE INVENTION

In accordance with the present invention O-acylated derivatives of 1,5-dideoxy-1,5-imino-D-glucitol and their N-alkyl, N-acyl, and N-aroyl derivatives are provided which have useful antiviral activity.

1,5-dideoxy-1,5-imino-D-glucitol is a six-membered heterocyclic compound having nitrogen in the ring and four hydroxyl groups. It is thus described by a systematic chemical name as a sugar derivative in which the six-membered ring is considered as a mimic of pyranose, with nitrogen instead of oxygen in the ring. It can also be described structurally as a derivative of piperidine. As defined herein, at least one and preferably all the free hydroxyl groups on 1,5-dideoxy-1,5-imino-D-glucitol and the N-substituted derivatives are O-acylated with carboxylic alkanoyl radicals selected from the group consisting of ω,ω,ω-trifluoro alkanoyl having from three to eight carbon atoms, carboxylic cycloalkanoyl groups having from four to eight carbon atoms and carboxylic acyclic alkanoyl groups having from two to ten carbon atoms. In these O-acylated derivatives the N-alkyl groups preferably contain from one to fourteen, and most preferably from four to ten, carbon atoms and the N-aroyl groups preferably contain from seven to fourteen carbon atoms.

The O-acyl groups are illustrated, e.g., by acetyl, propionoyl (propanoyl), butyryl (butanoyl), pentanoyl, hexanoyl, decanoyl, 4-methylpentanoyl, 2,2-dimethylpropanoyl, cyclopropylcarboxyl and 3-cyclopentylpropanoyl. Trifluoro-substituted O-acyl groups also are useful, e.g., 4,4,4-trifluorobutanoyl, 6,6,6-trifluorohexanoyl and 8,8,8-trifluorooctanoyl.

The N-alkyl groups are illustrated, e.g., by butyl, pentyl, hexyl, nonyl, 2-ethylbutyl and 2-methylpentyl. Trifluoro-substituted N-alkyl groups are also useful, e.g., 4,4,4-trifluorobutyl, 6,6,6-trifluorohexyl and 8,8,8-trifluorooctyl.

The N-acyl groups are illustrated, e.g., by methyl malonyl and ethyl malonyl.

The N-aroyl groups are illustrated, e.g., by phenylacetyl, benzyloxycarbonyl, benzoyl, biphenylacetyl, phenoxyacetyl, chlorophenylacetyl, hydrocinnamoyl, cinnamoyl and nicotinoyl.

Other useful N-aroyl groups are, e.g., p-decylbenzoyl, 3-(p-chlorophenoxy)propanoyl, acetylsalicyloyl or 2-(acetyloxy)benzoyl, 4-biphenylcarbonyl or (1,1'-biphenyl)-4-ylcarbonyl, 2-thiopheneacetyl, trans-3-furanacryloyl, 3-methoxyphenylacetyl and 3(trifluoromethyl)benzoyl.

The N-aroyl groups can have one or more, preferably 1 to 3, identical or different substituents in any position on the ring. Examples of substituents are alkyl having from one to ten carbon atoms such as methyl, ethyl, propyl and the like; alkoxy having from one to six carbon atoms such as methoxy, ethoxy, propoxy and the like; halogen such as Cl, Br or F; trifluoromethyl; phenyl; nitro; and hydroxyl. Illustrative examples of the antiviral O-acylated derivatives of 1,5-dideoxy-1,5-imino-D-glucitol and their N-alkyl, N-acyl and N-aroyl derivatives are the following:

1,5-(Benzyloxycarbonylimino)-1,5-dideoxy-D-glucitol, tetraacetate,
1,5-(Phenylacetylimino)-1,5-dideoxy-D-glucitol, tetraacetate,
1,5-(Benzoylimino)-1,5-dideoxy-D-glucitol, tetraacetate,
1,5-(Butylimino)-1,5-dideoxy-D-glucitol, tetraacetate,
1,5-(Ethyl malonylimino)-1,5-dideoxy-D-glucitol, tetraacetate,
1,5-(Hexylimino)-1,5-dideoxy-D-glucitol, tetraacetate,
1,5-(Nonylimino)-1,5-dideoxy-D-glucitol, tetraacetate,
1,5-(Benzyloxycarbonylimino)-1,5-dideoxy-D-glucitol, tetraisobutyrate,
1,5-(Butylimino)-1,5-dideoxy-D-glucitol, tetrabutyrate,
1,5-(Butylimino)-1,5-dideoxy-D-glucitol, tetrapropionate,
1,5-(Butylimino)-1,5-dideoxy-D-glucitol, tetrabenzoate,
1,5-Dideoxy-1,5-imino-D-glucitol, tetraisobutyrate,
1,5-(Hydrocinnamoylimino)-1,5-dideoxy-D-glucitol, tetraacetate,
1,5-(Methyl malonylimino)-1,5-dideoxy-D-glucitol, tetraacetate,
1,5-(Butylimino)-1,5-dideoxy-D-glucitol, tetraisobutyrate,
1,5-(Butylimino)-1,5-dideoxy-4R,6-O-(phenylmethylene)-D-glucitol, diacetate,
1,5-[(Phenoxymethyl) carbonylimino]-1,5-dideoxy-D-glucitol, tetraacetate,
1,5-[(2-Ethylbutyl)imino]-1,5-dideoxy-D-glucitol, tetraacetate,
1,5-(Butylimino)-1,5-dideoxy-D-glucitol, 2,3-diacetate,
1,5-(Hexylimino)-1,5-dideoxy-4R,6-O-(phenylmethylene)-D-glucitol, diacetate,
1,5-(Hexylimino)-1,5-dideoxy-D-glucitol, 2,3-diacetate,
1,5-[(2-Methylpentyl)imino]-1,5-dideoxy-D-glucitol, tetraacetate,
1,5-(Butylimino)-1,5-dideoxy-D-glucitol, 6-acetate,
1,5-[(3-Nicotinoyl)imino]-1,5-dideoxy-D-glucitol, tetraacetate,
1,5-(Cinnamoylimino)-1,5-dideoxy-D-glucitol, tetraacetate,
1,5-(Butylimino)-1,5-dideoxy-D-glucitol, 2,3-dibutyrate,
1,5-(Phenylacetylimino)-1,5-dideoxy-D-glucitol, tetraisobutyrate,
1,5-[(4-Chlorophenyl) acetylimino]-1,5-dideoxy-D-glucitol, tetraacetate,
1,5-[(4-Biphenyl)acetylimino]-1,5-dideoxy-D-glucitol, tetraacetate,
1,5-(Benzyloxycarbonylimino)-1,5-dideoxy-D-glucitol, tetrabutyrate, and
1,5-Dideoxy-1,5-imino-D-glucitol, tetrabutyrate.

Other illustrative examples of the O-acylated derivatives of 1,5-dideoxy-1,5-imino-D-glucitol and their N-alkyl and N-aroyl derivatives are the following:

1,5-(Butylimino)-1,5-dideoxy-D-glucitol, tetra(4,4,4-trifluorobutanoate),
1,5-[(4-Decylbenzoyl)imino]-1,5-dideoxy-D-glucitol, tetraacetate,
1,5-(Butylimino)-1,5-dideoxy-D-glucitol, tetrahexanoate,
1,5-(Butylimino)-1,5-dideoxy-D-glucitol, tetra(4-methylpentanoate),
1,5-(Butylimino)1,5-dideoxy-D-glucitol, tetra(2,2-dimethylpropanoate),
1,5-(Butylimino)-1,5-dideoxy-D-glucitol, 2,4,6-tri(2,2-dimethylpropanoate),
1,5-Dideoxy-1,5-[[3-(4-chlorophenoxy)-1-oxopropyl]imino]-D-glucitol, tetraacetate,
1,5-[[2-(Acetyloxy)benzoyl]imino]-1,5-dideoxy-D-glucitol, tetrabutanoate,
1,5-[([1,1,-biphenyl]-4-ylcarbonyl)imino]-1,5-dideoxy-D-glucitol, tetraacetate,
1,5-(Butylimino)-1,5-dideoxy-D-glucitol, tetra(cyclopropylcarboxylate),
1,5-Dideoxy-1,5-[[1-oxo-2-(2-thienyl)ethyl]imino]-D-glucitol, tetrabutanoate,
1,5-(Butylimino)-1,5-dideoxy-D-glucitol, tetra(3-cyclopentylpropanoate),
1,5-(Butylimino)-1,5-dideoxy-D-glucitol, tetradecanoate,
1,5-Dideoxy-1,5-[[3-(3-furanyl)-1-oxo-2E-propenyl]imino]-D-glucitol, tetrabutanoate,
1,5-(8,8,8-Trifluorooctylimino)-1,5-dideoxy-D-glucitol, tetrabutyrate,
1,5-(4,4,4-Trifluorobutylimino)-1,5-dideoxy-D-glucitol, tetraacetate,
1,5-(4,4,4-Trifluorobutylimino)-1,5-dideoxy-D-glucitol, tetraisobutyrate,
1,5-(6,6,6-Trifluorohexylimino)-1,5-dideoxy-D-glucitol, tetraburyrate,
1,5-(6,6,6-Trifluorohexylimino)-1,5-dideoxy-D-glucitol, 2,3,6-tributyrate,
1,5-(6,6,6-Trifluorohexylimino)-1,5-dideoxy-D-glucitol, 2,4,6-tributyrate.
1,5-Dideoxy-1,5-[[2-(3-methoxyphenyl)-1-oxoethyl]imino]-D-glucitol, tetrabutranoate and
1,5-Dideoxy-1,5-[[3-(trifluoromethyl)benzoyl]imino]-D-glucitol, tetrabutanoate.

The O-acylated derivatives of 1,5-dideoxy-1,5-imino-D-glucitol preferably contain an N-alkyl or N-aroyl radical in which from one to four of the free hydroxyl groups are O-acylated with carboxylic alkanoyl radicals selected from the group consisting of $\omega,\omega,\omega$-trifluoro alkanoyl having from three to eight carbon atoms, carboxylic cycloalkanoyl groups having from four to eight carbon atoms and carboxylic acyclic alkanoyl groups having from two to ten carbon atoms, wherein the N-aroyl radical is selected from the group consisting of p-decylbenzoyl, 3-(p-chlorophenoxy)propanoyl, 2-(acetyloxy)benzoyl, [1,1'-biphenyl]-4-ylcarbonyl, 2-thiopheneacetyl, trans-3-furanacryloyl, 3-methoxyphenylacetyl and 3-(trifluoromethyl)benzoyl, and wherein the N-alkyl contains from one to fourteen carbon atoms, provided that when N-alkyl contains from one to five carbon atoms the O-acylated groups are $\omega,\omega,\omega$-trifluoro alkanoyl or carboxylic cycloalkanoyl.

Especially preferred are the following four groups of O-acylated derivatives of 1,5-dideoxy-1,5-imino-D-glucitol:

I. An O-acylated derivative of 1,5-dideoxy-1,5-imino-D-glucitol containing an N-aroyl radical selected from the group consisting of p-decylbenzoyl, 3-(p-chlorophenoxy)propanoyl, 2-(acetyloxy)benzoyl, [1,1'-biphenyl]-4-ylcarbonyl, 2-thiopheneacetyl, trans-3-furanacryloyl, 3-methoxyphenylacetyl and 3-(trifluoromethyl)benzoyl, and in which from one to four of the free hydroxyl groups are O-acylated with carboxylic acyclic alkanoyl groups having from two to ten carbon atoms.

II. An O-acylated derivative of 1,5-dideoxy-1,5-imino-D-glucitol containing an N-alkyl group in which from one to four of the free hydroxyl groups are O-acylated with ω,ω,ω-trifluoroalkanoyl having from three to eight carbon atoms or with carboxylic cycloalkanoyl groups having from four to eight carbon atoms and in which the N-alkyl groups contain from one to eight carbon atoms.

III. An O-acylated derivative of 1,5-dideoxy-1,5-imino-D-glucitol containing an N-alkyl group in which from one to four of the free hydroxyl groups are O-acylated with carboxylic acyclic alkanoyl groups having from two to ten carbon atoms and in which the N-alkyl groups contain from six to fourteen carbon atoms.

IV. An O-acylated derivative of 1,5-dideoxy-1,5-imino-D-glucitol containing an N-ω,ω,ω-trifluoro-alkyl group having from three to eight carbon atoms and in which from one to four of the free hydroxyl groups are O-acylated with carboxylic acyclic alkanoyl groups having from two to ten carbon atoms.

These novel antiviral compounds can be prepared from the amine, 1,5-dideoxy-1,5-imino-D-glucitol, by conventional N-alkylation or N-acylation with appropriate alkyl, acyl or aroyl groups. The free hydroxyl groups on the amine can be acylated either before or after this N-alkylation or N-acylation. See the illustrative reaction schemes set forth hereinbelow.

In preferred embodiments alkylation can be carried out by reaction of the starting amine with an appropriate alkylaldehyde or an appropriate arylaldehyde. Illustrative alkylaldehydes are butyraldehyde, ethylbutyraldehyde, 2-methylvaleraldehyde, caproaldehyde, and nonylaldehyde. Illustrative arylaldehydes are, e.g., benzaldehyde, ethylbenzaldehyde and hydrocinnamaldehyde.

Alternatively, reaction of the starting amine with benzyl chloroformate can be carried out to give N-benzyloxycarbonyl derivatives of the amine.

Acylation of the free hydroxyl groups is conveniently carried out by reaction of the amine with an appropriate acid anhydride such as, e.g., the acetic-, propionic-, butyric-, isobutyric- and benzoic anhydrides.

In other preferred embodiments, the pre-acylated amine can be reacted with alkylating or acylating agents to form the N-alkyl, N-acyl and N-aroyl derivatives. Illustrative of such alkylating agents are, e.g., benzoyl chloride or phenylacetic anhydride together with triethylamine. Illustrative of such acylating agents are methyl malonyl chloride and ethyl malonyl chloride.

Although specific methods of production are described herein, it will be appreciated that the novel antiviral compounds claimed herein are not limited to any particular method of production.

The foregoing compounds can be demonstrated to have inhibitory activity against visna virus in a conventional plaque reduction assay. Visna virus, a lentivirus genetically very similar to the AIDS virus, is pathogenic for sheep and goats. See Sonigo et al., *Cell* 42,369–382 (1985); Haase, *Nature* 322,130–136 (1986). Inhibition of visna virus replication in vitro as a useful model for human immunodeficiency virus (HIV) and its inhibition by test compounds has been described by Frank et al., *Antimicrobial Agents and Chemotherapy* 31 (9), 1369–1374 (1987). The N-butyl derivative of 1,5-dideoxy-1,5-imino-D-glucitol, also referred to as n-butyl-deoxynojirimycin (N-Bu-DNJ), was used as a control standard for comparison with various novel compounds of this invention. The HIV inhibitory activity of N-Bu-DNJ is described in U.S. Pat. No. 4,849,430.

Inhibitory activity can also be demonstrated by the acylated derivatives against alpha- and beta-glucosidase enzymes. In some cases, the non-acylated derivatives also have effective inhibitory activity against visna virus, cytomegalovirus (CMV) and/or the alpha- and betaglucosidases.

DETAILED DESCRIPTION OF THE INVENTION

The following detailed examples will further illustrate the invention although it will be understood that the invention is not limited to these specific examples.

EXAMPLE 1

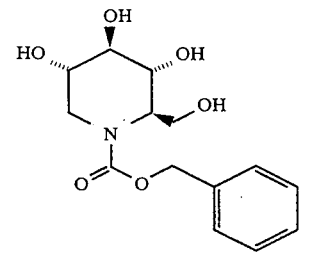

1,5-(Benzyloxycarbonylimino)-1,5-dideoxy-D-glucitol.

Benzyl chloroformate (1.15g, 0.00674 mole was added to a solution of 1,5-dideoxy-1,5-imino-D-glucitol (1.0g, 0.00613 mole), in 50 ml saturated aqueous sodium hydrogen carbonate and stirred for 20 hrs. at room temperature. The product was extracted into ethyl acetate (3×75 ml), dried over anhydrous sodium sulfate, filtered and concentrated in vacuo to an oil. Chromatography on silical gel gave the title compound (1.2 g). Structure assignment was supported by NMR and infrared spectra and by elemental analysis. Analysis calcd. for $C_{14}H_{19}NO_6$: C, 56.56; H, 6.44; N, 4.71. Found: C, 56.29; H, 6.62; N, 4.53.

EXAMPLE 2

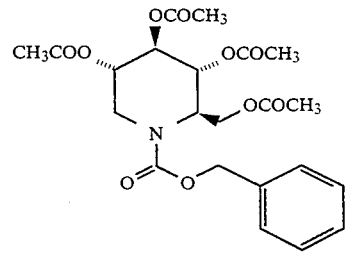

1,5-(Benzyloxycarbonylimino)-1,5-dideoxy-D-glucitol, tetraacetate.

To a solution of the title product of Example 1 (491 mg, 1.65 moles) in 5 ml of pyridine was added 2 ml of acetic anhydride. The resulting mixture was stirred for 15 minutes at room temperature and then at reflux for 5 minutes. After cooling, the mixture was poured into 25 ml of ice water and extracted with three portions of ethyl acetate. The combined organic extracts were washed with dilute hydrochloric acid, dried over sodium sulfate, filtered, and the solvent removed on a rotary evaporator. Chromatography on silica gel using a gradient of 25 to 100% ethyl acetate-hexane as eluant gave the title compound (510 mg) as an oil. Analysis for $C_{22}H_{27}NO_{10}$ (MW 465.46):

Calcd. C, 56.76; H, 5.85; N, 3.01. Found: C, 56.72; H, 5.82; N, 3.02.

EXAMPLE 3

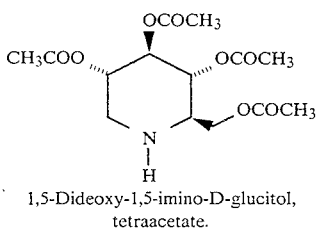

1,5-Dideoxy-1,5-imino-D-glucitol, tetraacetate.

The title compound of Example 2 (13.417g, 0.029 moles) was hydrogenated (5 psi, room temperature 2 hrs.) in 250 ml of methanol containing 4% Pd/C (3.0g). This mixture was filtered and concentrated in vacuo to give an oil. Chromatography on silica gel gave the title compound as a waxy solid. Structure assignment was supported by NMR, infrared spectra and elemental analysis.

Analysis calcd. for $Cl_{14}H_{21}NO_8$: C, 50.75; H, 6.39; N, 4.23. Found: C, 50.53; H, 6.41; N, 4.14.

EXAMPLE 4

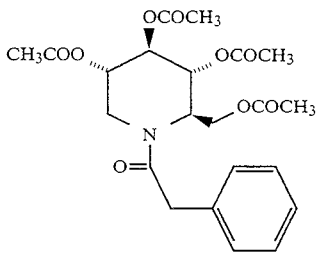

1,5-(Phenylacetylimino)-1,5-dideoxy-D-glucitol-tetraacetate.

Phenylacetyl chloride (0.23g, 0.0015 mole) was added to a cold (−76° C., solution of the title compound of Example 3 (0.5 g, 0.0015 mole) in 30 ml tetrahydrofuran. Triethylamine (0.5 ml) was added and the solution stirred for 20 hrs at room temperature. Triethylamine hydrochloride was removed by filtration and the filtrate concentrated in vacuo to give 0.81 g of an oil. Chromatography on silica gel and recrystallizing from ethyl acetate/hexane gave the title product, m.p. 98°-100° C. Structure assignment was supported by NMR, infrared spectra and elemental analysis.

Analysis calcd. for $C_{22}H_{27}NO_9$: C, 58.79; H, 6.05; N, 3.12. Found: C, 58.74; H, 6.12; N, 3.14.

EXAMPLE 5

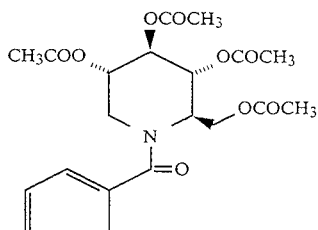

1,5-(Benzoylimino)-1,5-dideoxy-D-glucitol, tetraacetate.

The title compound, m.p. pa. 138° C., was prepared by the method of Example 4 using benzoyl chloride instead of phenylacetyl chloride. Structure assignment was supported by NMR, infrared spectra and elemental analysis.

Analysis calcd. for $C_{21}H_{25}NO_9$: C, 57.93; H, 5.79; N, 3.22. Found: C, 57.88; H, 5.82; N, 3.30.

EXAMPLE 6

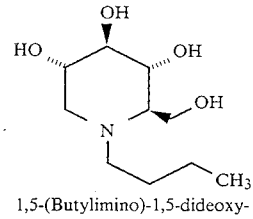

1,5-(Butylimino)-1,5-dideoxy-D-glucitol.

A solution of 1,5-dideoxy-1,5-imino-D-glucitol (5.14 g, 0.0315 mole), butyraldehyde (3.35 ml, 0.0380 mole) and Pd black (1 g) in 200 ml methanol was hydrogenated (60 psi/29° C./21 hrs.). After filtering the resulting mixture, the filtrate was concentrated in vacuo to an oil. The title compound was crystallized from acetone and recrystallized from methanol/acetone, m.p. ca. 132° C. Structure assignment was supported by NMR, infrared spectra and elemental analysis.

Analysis calcd. for $C_{10}H_{21}NO_4$: C, 54.78; H, 9.65; N, 6.39. Found: C, 54.46; H, 9.33; N, 6.46.

EXAMPLE 7

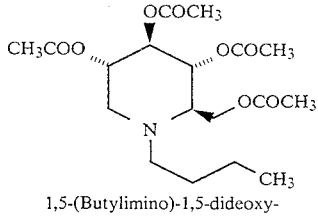

1,5-(Butylimino)-1,5-dideoxy-D-glucitol, tetraacetate.

Acetic anhydride (1.08g, 0.0106 mole) was added to the title compound of Example 6 (0.50 g, 0.0023 mole) in 5 ml pyridine and stirred for 17 days at room temperature. The product was evaporated under nitrogen gas. The resulting title compound was purified by silica gel chromatography. Structure assignment was supported by NMR, infrared spectra and elemental analysis.

Analysis calcd. for $C_{18}H_{29}NO_8$: C, 55.80; H, 7.54; N, 3.62. Found: C, 55.42; H, 7.50; N, 3.72.

EXAMPLE 8

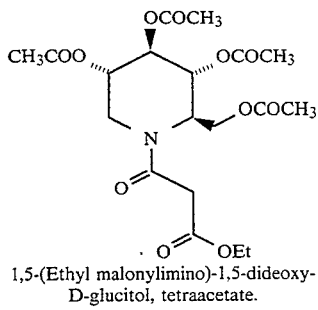

1,5-(Ethyl malonylimino)-1,5-dideoxy-
D-glucitol, tetraacetate.

Ethyl malonyl chloride (0.5 g, 0.0033 mole) in 10 ml tetrahydrofuran was added to a cold (0° C.) solution of the title compound of Example 3 (1.0 g, 0.0030 mole) in 30 ml tetrahydrofuran. After stirring for 30 min. a solution of triethylamine (0.67 g, 0.0066 mole) in 10 ml tetrahydrofuran was added. The mixture was allowed to come to room temperature and stirred for 20 hrs. Triethylamine hydrochloride was removed by filtration and the filtrate concentrated in vacuo to give an oil. Chromatography on silica gel gave the title compound as a clear oil. Structure assignment was supported by NMR, infrared spectra and elemental analysis.

Analysis calcd. for $C_{19}H_{27}NO_{11}$: C, 51.23; H, 6.11; N, 3.14. Found: C, 50.99; H, 6.14; N, 3.13.

EXAMPLE 9

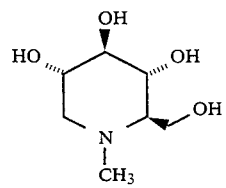

1,5-(Methylimino)-1,5-dideoxy-D-glucitol

A solution of 1,5-dideoxy-1,5-imino-D-glucitol (7.5g, 0,046 mole), formaldehyde (37%, 26.0g, 0.322 mole) and 5% Palladium black in 300 ml methanol was hydrogenated (60 psi/25° C./20 hrs). After filtering the resulting mixture, the filtrate was concentrated to give a foam. The product was crystallized from methanol-acetone to give a white solid. Structure assignment was supported by NMR, infrared spectra and elemental analysis.

Analysis calcd. for $C_7H_{15}NO_4$: C, 47.45; H, 8.53; N, 7.91. Found: C, 47.24; H, 8.66; N, 7.83.

EXAMPLE 10

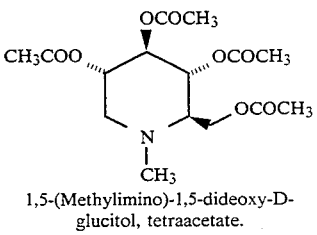

1,5-(Methylimino)-1,5-dideoxy-D-
glucitol, tetraacetate.

Acetic anhydride (0.69 g, 0.0068 mole) was added to the title compound of Example 9 (0.20 g, 0.0011 mole) in 10 ml pyridine and stirred at room temperature for 5 days. The product was concentrated with a gentle flow of nitrogen gas. The residue was dissolved in 25 ml ethyl acetate, washed with water, dried over sodium sulfate, filtered and concentrated to an oil. The product was purified by silica gel chromatography and recrystallized from ethyl acetate -hexane (m.p. 102° C.). Structure assignment was supported by NMR, infrared spectra and elemental analysis.

Analysis calcd. for $C_{15}H_{23}NO_8$: C, 52.17; H, 6.71; N, 4.06. Found: C, 52.15; H, 6.72; N, 3.97.

EXAMPLE 11

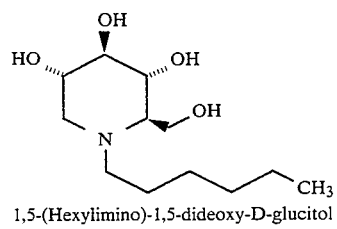

1,5-(Hexylimino)-1,5-dideoxy-D-glucitol

A mixture of 1,5-dideoxy-1,5-imino-D-glucitol (0.5 g, 0.0031 moles), caproaldehyde (0.45 g, 0.0045 mole) and 5% Palladium black (0.1 g) in methanol (105 ml) was hydrogenated (5 psi/25° C./5 days). After filtering the resulting mixture, the filtrate was concentrated with a flow of nitrogen to give an oily solid. The title compound was crystallized from acetone-ethanol, DSC ca. 115° C. Structure assignment was supported by NMR, infrared spectra and elemental analysis.

Analysis calcd. for $C_{12}H_{25}NO_4$: C, 58.27; H, 10.19; N, 5.66. Found: C, 58.19; H, 10.24; N, 5.65.

EXAMPLE 12

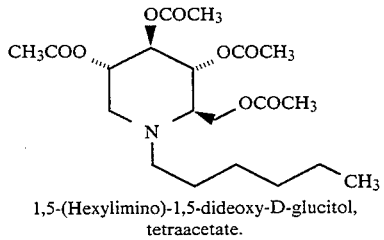

1,5-(Hexylimino)-1,5-dideoxy-D-glucitol,
tetraacetate.

The title compound was prepared by the Method of Example 10 utilizing the product of Example 11 instead of 1,5-(methylimino)-1,5-dideoxy-D-glucitol. The structure assignment was supported by NMR, infrared spectra and elemental analysis.

Analysis calcd. for $C_{20}H_{33}NO_8$: C, 57.82; H, 8.01; N, 3.37. Found: C, 57.73; H, 7.83; N, 3.36.

EXAMPLE 13

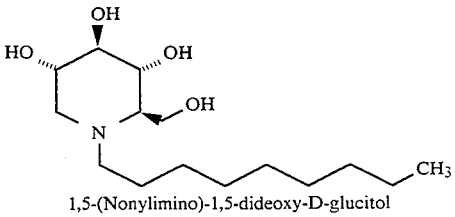

1,5-(Nonylimino)-1,5-dideoxy-D-glucitol

A solution of 1,5-dideoxy-1,5-imino-D-glucitol (0.5 g, 0.0031 mole); nonyl aldehyde (0.52 g, 0.0037 mole) and 5% Pd black (0.1 g) in methanol (100 ml) was hydrogenated (60 psi/25° C./46 hrs.). After filtering the resulting mixture, the filtrate was concentrated with a gentle flow of nitrogen to an oily solid. This material was stirred with a small amount of acetone and the solid filtered. Recrystallization from ethanol—acetone gave the title compound, DSC ca. 109° C. Structure assignment was supported by NMR, infrared spectra and elemental analysis. Analysis calcd. for $C_{15}H_{31}NO_4$: C, 62.25; H, 10.80; N, 4.84. Found: C, 62.15; H, 10.86; N, 4.79.

EXAMPLE 14

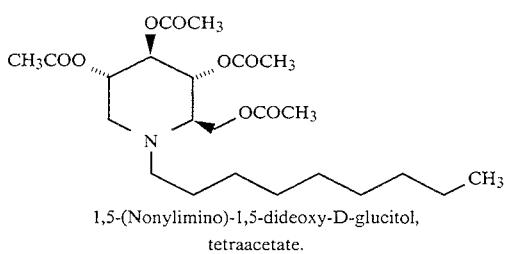

1,5-(Nonylimino)-1,5-dideoxy-D-glucitol, tetraacetate.

The title compound was prepared by the Method of Example 10 utilizing the product of Example 13 instead of 1,5-(methylimino)-1,5-dideoxy-D-glucitol. The structure assignment was supported by NMR, infrared spectra and elemental analysis.

Analysis calcd. for $C_{23}H_{39}NO_8$: C, 60.37; H, 8.59; N, 3.06. Found: C, 60.19; H, 7.99; N, 3.12.

EXAMPLE 15

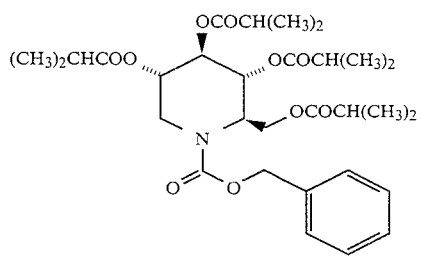

1,5-(Benzyloxycarbonylimino)-1,5-dideoxy-D-glucitol, tetraisobutyrate.

To a solution of the title product of Example 1 (2.0 g, 0.0067 mole) in 30 ml pyridine was added isobutyric anhydride (6.4 g, 0.0436 mole) and stirred at room temperature for 6 days. The reaction was poured into 150 ml water, stirred for 20 hrs. and extracted with two portions of ethyl acetate (2×100 ml). The combined organic extracts were washed with water (4×75 ml), dried over sodium sulfate, filtered, and the solvent removed on a rotary evaporator to give an oil. The title compound was purified by silica gel chromatography. The structure assignment was supported by NMR, infrared spectra and elemental analysis.

Analysis calcd. for $C_{30}H_{43}NO_{10}$: C, 62.38; H, 7.50; N, 2.42. Found: C, 62.23; H, 7.60; N, 2.44.

EXAMPLE 16

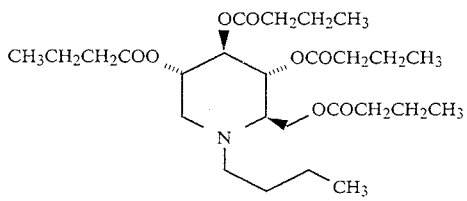

1,5-(Butylimino)-1,5-dideoxy-D-glucitol, tetrabutyrate.

The title compound was prepared by the Method of Example 7 using n-butyric anhydride instead of acetic anhydride. After purification by silica gel chromatography the product was crystallized from pentane. The structure assignment was supported by NMR, infrared spectra and elemental analysis.

Analysis calcd. for $C_{26}H_{45}NO_8$: C, 62.50; H, 9.08; N, 2.80. Found: C, 62.48; H, 9.12; N, 2.84.

EXAMPLE 17

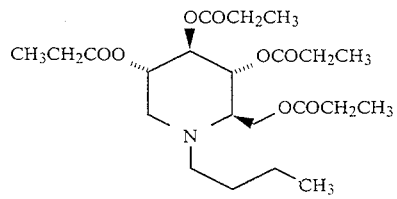

1,5-(Butylimino)-1,5-dideoxy-D-glucitol, tetrapropionate.

The title compound was prepared by the Method of Example 7 substituting propionic anhydride for acetic anhydride. The structure was supported by NMR, infrared spectra and elemental analysis.

Analysis calcd. for $C_{22}H_{37}NO_8$: C, 59.58; H, 8.41; N, 3.16. Found: C, 59.56; H, 8.68; N, 3.19.

EXAMPLE 18

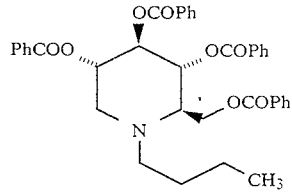

1,5-(Butylimino)-1,5-dideoxy-D-glucitol, tetrabenzoate.

The title compound was prepared by the Method of Example 7 substituting benzoic anhydride for acetic anhydride. The reaction was allowed to stir at room temperature for 27 days. The structure assignment was supported by NMR, infrared spectra and elemental analysis. Analysis calcd. for $C_{38}H_{37}NO_8$: C, 71.80; H, 5.87; N, 2.20. Found: C, 71.49; H, 5.92; N, 2.24.

EXAMPLE 19

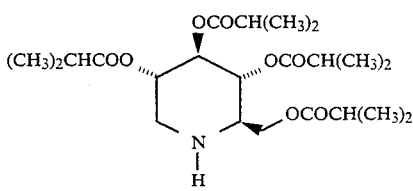

1,5-Dideoxy-1,5-imino-D-glucitol, tetraisobutyrate.

The title compound of Example 15 (2.65 g, 0.0046 mole) was hydrogenated (15 psi, room temperature, 4 hr.) in 100 ml methanol containing 5% Pd/C. This mixture was filtered and concentrated by a rotary evaporator to a solid which was recrystallized from ethyl acetate-hexane (DSC 63° C.). Assignment was supported by NMR, infrared spectra and elemental analysis.

Analysis calcd. for $C_{22}H_{37}NO_8$: C, 59.58; H, 8.41; N, 3.16. Found: C, 59.49; H, 8.46; N, 3.17.

EXAMPLE 20

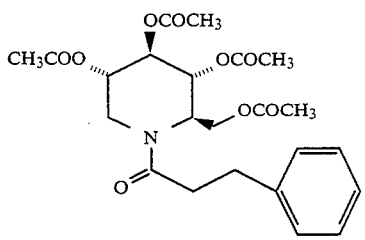

1,5-(Hydrocinnamoylimino)-1,5-dideoxy-D-glucitol, tetraacetate.

By the Method of Example 4 and substituting hydrocinnamoyl chloride for phenylacetyl chloride the title compound was prepared. Structure assignment was supported by NMR, infrared spectra and elemental analysis.

Analysis calcd. for $C_{23}H_{29}NO_9$: C, 59.60; H, 6.31; N, 3.02. Found: C, 59.49; H, 6.25; N, 3.08.

EXAMPLE 21

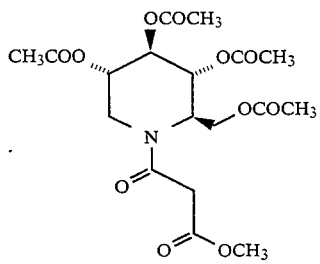

1,5-(Methyl malonylimino)-1,5-dideoxy-D-glucitol, tetraacetate.

The title compound was prepared by the Method of Example 8 and substituting methyl malonyl chloride for ethyl malonyl chloride. The structure assignment was supported by NMR, infrared spectra and elemental analysis.

Analysis calcd. for $C_{18}H_{25}NO_{11}$: C, 50.12; H, 5.84; N, 3.25. Found: C, 49.91; H, 5.82; N, 3.13.

EXAMPLE 22

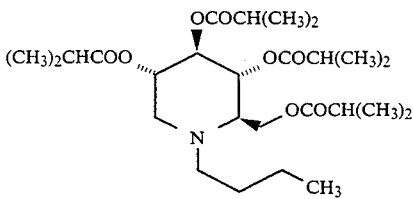

1,5-(Butylimino)-1,5-dideoxy-D-glucitol, tetraisobutyrate.

The title compound was prepared by the Method of Example 7 and substituting isobutyric anhydride for acetic anhydride, m.p. 59° C. The structure was supported by NMR, infrared spectra and elemental analysis.

Analysis calcd. for $C_{26}H_{45}NO_8$: C, 62.50; H, 9.08; N, 2.80. Found: C, 62.43; H, 9.24; N, 2.82.

EXAMPLE 23

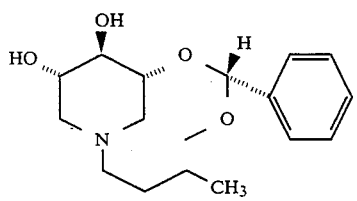

1,5-(Butylimino)-1,5-dideoxy-4R,6-O-(phenylmethylene)-D-glucitol.

p-Toluenesulfonic acid monohydrate (10.4 g, 0.055 mole) was added to a solution of dimethoxytoluene (20.8 g, 0.137 mole) in 150 ml of dimethylformamide. After stirring for 3.5 hrs, 1,5-(butylimino)-1,5-dideoxy-D-glucitol (10.0 g, 0.046 mole) was added and the solution was stirred at room temperature for 18 days. The reaction was concentrated on a rotary evaporator. The residue was passed through a column containing Amberlite IRA-400 ion exchange resin with methanol. The eluant was concentrated to a brown oil. The title compound was purified by silica gel chromatography and crystallized from ethyl acetatehexane (DSC 118° C.). The structure assignment was supported by NMR, infrared spectra and elemental analysis.

Analysis calcd. for $C_{17}H_{25}NO_4$: C, 66.43; H, 8.20; N, 4.56. Found: C, 66.38; H, 8.20; N, 4.52.

EXAMPLE 24

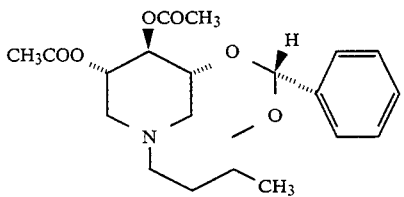

1,5-(Butylimino)-1,5-dideoxy-4R,6-O-(phenylmethylene)-D-glucitol, diacetate.

Acetic anhydride (0.30 g, 0.0029 mole) was added to the product of Example 23 (0.30 g, 0,001 mole) in 10 ml pyridine and stirred for 5 days at room temperature. Water (5 ml) was added and the solution stirred for 1 hr. After removal of the solvent by a rotary evaporator, the product was purified by silica gel chromatography and recrystallized from ethyl acetate-hexane (DSC 126° C.). Structure assignment was supported by NMR, infrared spectra and elemental analysis.

Analysis calcd. for $C_{21}H_{29}NO_6$: C, 64.43; H, 7.47; N, 3.58. Found: C, 64.39; H, 7.70; N, 3.53.

EXAMPLE 25

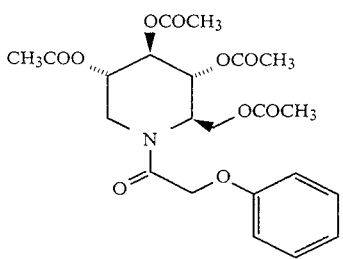

1,5-[(Phenoxymethyl)carbonylimino]-1,5-dideoxy-D-glucitol, tetraacetate.

The title compound was prepared by the Method of Example 4 and substituting phenoxyacetyl chloride for phenylacetyl chloride (DSC, 219° C.). Structure assignment was supported by NMR, infrared spectra and elemental analysis.

Analysis calcd. for $C_{22}H_{27}NO_{10}$: C, 56.77; H, 5.85; N, 3.01. Found: C, 56.81; H, 5.83; N, 3.21.

EXAMPLE 26

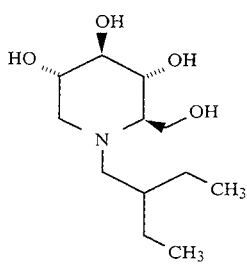

1,5-[(2-Ethylbutyl)imino]-1,5-dideoxy-D-glucitol

A solution of 1,5-dideoxy-1,5-imino-D-glucitol (0.99 g, 0.0061 mole), 2-ethylbutyraldehyde (0.98 g, 0.0098 mole) and 5% Pd black in methanol (68 ml), tetrahydrofuran (34 ml) and water (17 ml) was hydrogenated (5 psi/25° C./72 hrs.). After filtering the resulting mixture, the filtrate was concentrated to an oily solid. This residue was dissolved in methanol (40 ml) and cooled. The white solid was removed by filtration to give as 1,5-dideoxy-1,5-imino-D-glucitol. The filtrate was concentrated to an oil. The product was purified by silica gel chromatography to give a white solid. Recrystallization from methanol-ethyl acetate gave the title compound, DSC ca. 95° C. Structural assignment was supported by NMR, infrared spectra and elemental analysis.

Analysis calcd. for $C_{12}H_{25}NO_4$: C, 58.27; H, 10.19; N, 5.66. Found: C, 57.89; H, 10.09; N, 5.69.

EXAMPLE 27

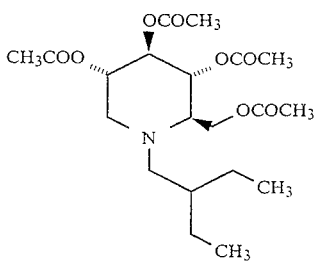

1,5-[(2-Ethylbutyl)imino]-1,5-dideoxy-D-glucitol, tetraacetate.

The title compound was prepared by the Method of Example 7 and substituting 1,5-[(2-ethyl-butyl)imino]-1,5-dideoxy-D-glucitol for 1,5-(butylimino)-1,5-dideoxy-D-glucitol. Structure assignment was supported by NMR, infrared spectra and elemental analysis.

Analysis calcd. for $C_{20}H_{33}NO_8$: C, 57.82; H, 8.01; N, 3.37. Found: C, 57.42; H, 7.92; N, 3.31.

EXAMPLE 28

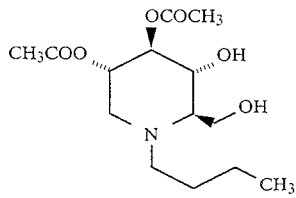

1,5-(Butylimino)-1,5-dideoxy-D-glucitol, 2,3-diacetate.

A mixture of the title compound of Example 24 (1.9 g, 0.0049 mole) and 20% Pd black (2.0 g) in methanol, tetrahydrofuran and methanol (6:4:2) was hydrogenated (60 psi/60° C./21 hr.). After filtering the resulting mixture, the filtrate was concentrated in vacuo to an oil. The product was purified by silica gel chromatography. Structure assignment was supported by NMR and elemental analysis.

Analysis calcd. for $C_{14}H_{25}NO_6$: C, 55.43; H, 8.31; N, 4.62. Found: C, 55.40; H, 8.38; N, 4.50.

EXAMPLE 29

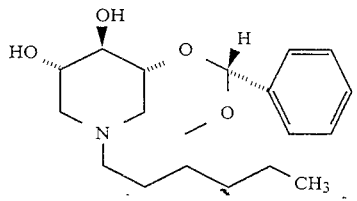

1,5-(Hexylimino)-1,5-dideoxy-4R,6-O-(phenylmethylene)-D-glucitol.

The title compound was prepared by the Method of Example 23 and substituting the product of Example 11 for 1,5-(butylimino)-1,5-dideoxy-D-glucitol (DSC 101° C.) Structure assignment was supported by NMR, infrared spectra and elemental analysis.

Analysis calcd. for $C_{19}H_{29}NO_4$: C, 68.03; H, 8.71; N, 4.18. Found: C, 68.04; H, 8.76; N, 4.15.

EXAMPLE 30

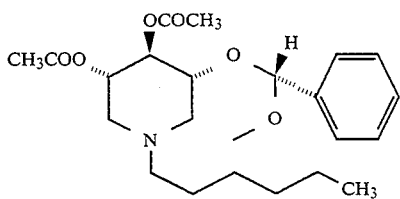

1,5-(Hexylimino)-1,5-dideoxy-4R,6-O-(phenylmethylene)-D-glucitol, 2,3-diacetate.

The title compound can be prepared by the Method of Example 24 and substituting the product of Example 29 for the product of Example 23.

EXAMPLE 31

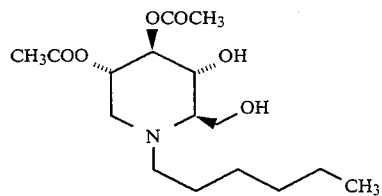

1,5-(Hexylimino)-1,5-dideoxy-D-glucitol, 2,3-diacetate.

The title compound can be prepared by the Method of Example 28 by substituting the product of Example 30 for the product of Example 24 in the synthesis reaction.

EXAMPLE 32

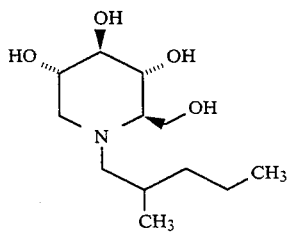

1,5-[(2-Methylpentyl)imino]-1,5-dideoxy-D-glucitol.

The title compound was prepared as a solid by the Method of Example 26 by using 2-methylvaleraldehyde instead of 2-ethylbutyraldehyde in the synthesis reaction. (DSC ca. 89° C.) The structure was supported by NMR; infrared spectra and mass spectroscopy.

EXAMPLE 33

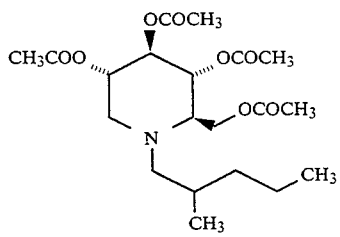

1,5-[(2-Methylpentyl)imino]-1,5-dideoxy-D-glucitol, tetraacetate.

The title compound was prepared by the Method of Example 7 by substituting 1,5-[(2-Methylpentyl)imino]-1,5-dideoxy-D-glucitol for 1,5-(butylimino)-1,5-dideoxy-D-glucitol in the synthesis reaction. The structure assignment was supported by CMR and NMR.

EXAMPLE 34

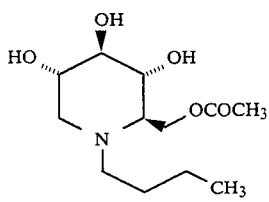

1,5-(Butylimino)-1,5-dideoxy-D-glucitol, 6-acetate.

Acetic anhydride (0.46 g, 0.0046 mole) was added to the title compound of Example 6 (1.0 g, 0.0046 mole) in 150 ml pyridine cooled to −40° C. by a dry ice/acetone bath. The reaction was allowed to come to room temperature and stirred for 20 hrs. Water (5 ml) was added and the reaction stirred for 1 hr. The solution was concentrated in vacuo to an oil. The title compound was purified by silica gel chromatography to give a solid which was recrystallized from methanol-ethyl acetate (DSC 131° C.). The structure assignment was supported by NMR, mass spectroscopy and elemental analysis.

Analysis calcd. for $C_{12}H_{23}NO_5 \cdot \frac{1}{3} H_2O$: C, 54.04; H, 8.92; N, 5.25. Found: C, 53.97; H, 9.04; N, 5.53.

EXAMPLE 35

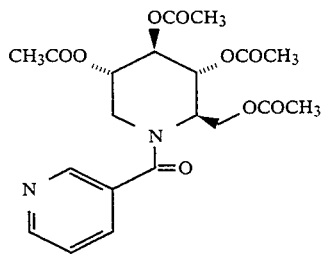

1,5-[(3-Nicotinoyl)imino]-1,5-dideoxy-D-glucitol, tetraacetate.

The title compound was prepared by the Method of Example 4 by substituting nicotinoyl chloride for phenylacetyl chloride in the synthesis reaction. Structure assignment was supported by NMR.

EXAMPLE 36

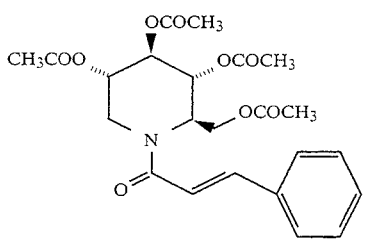

1,5-(Cinnamoylimino)-1,5-dideoxy-
D-glucitol, tetraacetate.

Triethylamine (0.5 ml) was added to a cold (0° C.) solution of 1,5-dideoxy-1,5-imino-D-glucitol (0.5 g, 0.0015 mole) and cinnamoyl chloride (0.25 g, 0.0015 mole) in 50 ml tetrahydrofuran. The mixture was allowed to come to room temperature and stirred for 3 days. The reaction mixture was concentrated in vacuo to an oily solid. Ethyl acetate was added to the residue and the solid removed by filtration. After concentrating the filtrate in vacuo, the title compound was purified by silica gel chromatography. The structure assignment was supported by NMR, infrared spectra and elemental analysis.

Analysis calcd. for $C_{23}H_{27}NO_9$: C, 59.86; H, 5.90; N, 3.04. Found: C, 59.66; H, 5.93; N, 2.99.

EXAMPLE 37

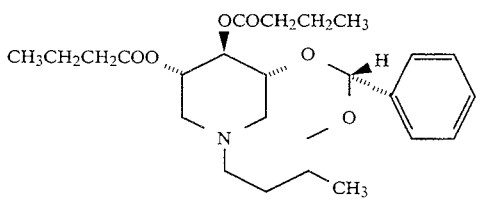

1,5-(Butylimino)-1,5-dideoxy-4R, 6-O-
(phenylmethylene)-D-glucitol, 2,3-dibutyrate.

The title compound was prepared by the Method of Example 24 by substituting butyric anhydride for acetic anhydride in the synthesis reaction. The structure assignment was supported by NMR, infrared spectra and elemental analysis.

Analysis calcd. for $C_{25}H_{37}NO_6$: C, 67.09; H, 8.33; N, 3.13. Found: C, 67.05; H, 8.44; N, 3.12.

EXAMPLE 38

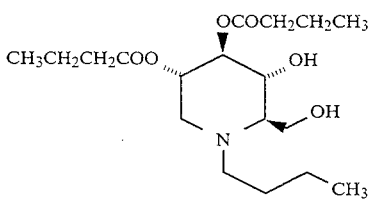

1,5-(Butylimino)-1,5-dideoxy-D-glucitol,
2,3-dibutyrate.

The title compound was prepared by the Method of Example 28 by substituting the title compound of Example 37 for the title compound of Example 24. Structure assignment was supported by NMR and elemental analysis.

Analysis calcd. for $C_{18}H_{33}NO_6$: C, 60.14; H, 9.25; N, 3.90. Found: C, 59.98; H, 9.38; N, 3.82.

EXAMPLE 39

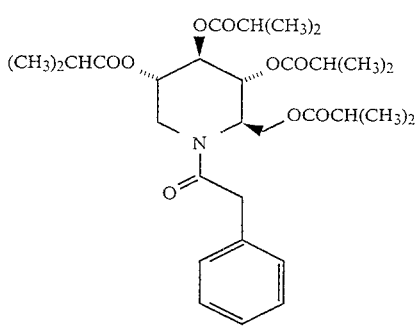

1,5-(Phenylacetylimino)-1,5-dideoxy-
D-glucitol, tetraisobutyrate.

The title compound was prepared by the Method of Example 4 by substituting the title product of Example 19 for the title product of Example 3 in the synthesis reaction. (DSC 96° C., from ethyl acetate-hexane.) The structure assignment was supported by NMR, infrared spectra and elemental analysis.

Analysis calcd. for $C_{30}H_{43}NO_9$: C; 64.15; H, 7.72; N, 2.49. Found: C, 64.15; H, 7.77; N, 2.30.

EXAMPLE 40

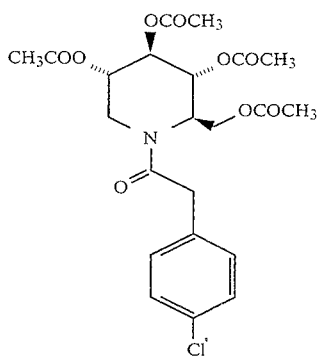

1,5-[(4-Chlorophenyl)acetylimino]-1, 5-
dideoxy-D-glucitol, tetraacetate.

The title compound was prepared by the Method of Example 4 by substituting para-chlorophenylacetyl chloride for phenylacetyl chloride in the synthesis reaction. The structure assignment was supported by NMR, infrared spectra and elemental analysis.

Analysis calcd. for $C_{22}H_{26}ClNO_9$: C, 54.61; H, 5.42; Cl, 7.33; N, 2.89. Found: C, 54.61; H, 5.45; Cl, 7.35; N, 2.88.

EXAMPLE 41

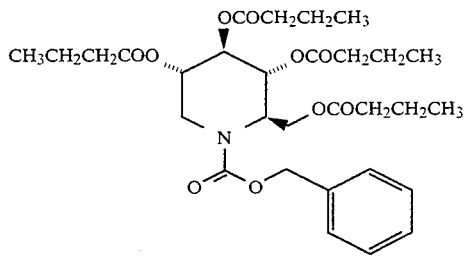

1,5-(Benzyloxycarbonylimino)-1,5-dideoxy-D-glucitol, tetrabutyrate.

The title compound was prepared by the Method of Example 15 by substituting butyric anhydride for isobutyric anhydride in the synthesis reaction. The structure assignment was supported by NMR, infrared spectra and elemental analysis.

Analysis calcd. for $C_{30}H_{43}NO_{10}$: C, 62.38; H, 7.50; N, 2.42. Found: C, 62.21; H, 7.52; N, 2.42.

EXAMPLE 42

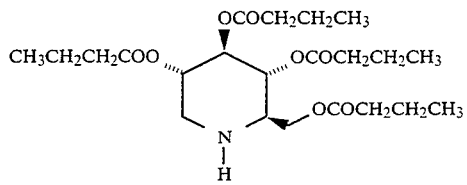

1,5-Dideoxy-1,5-imino-D-glucitol, tetrabutyrate.

The title compound was prepared by the Method of Example 19 and substituting the product of Example 41 for the product of Example 15. The structure assignment was supported by NMR, infrared spectra and elemental analysis.

Analysis calcd. for $C_{22}H_{37}NO_3$: C, 59.58; H, 8.41; N, 3.16. Found: C, 59.46; H, 8.52; N, 3.19.

EXAMPLE 43

Various compounds as prepared above were tested for inhibition of visna virus in vitro in a plaque reduction assay as follows:

METHOD

Cell and Virus Propagation

Sheep choroid plexus(SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at −70° C.

Plaque Reduction Assay

SCP cells were cultured in 6-well plates to confluence. Wells were washed two times with serum free Minimal Essential Medium (MEM) to remove FBS. 0.2ml of virus was added per well in MEM supplemented with 4mM glutamine and gentamycin. After 1 hour adsorption, the virus was aspirated from each well. The appropriate concentration of each compound in 5 ml of Medium 199 (M-199) supplemented with 2% lamb serum, 4mM glutamine, 0.5% agarose and gentamycin was added to each well. Cultures were incubated at 37° C. in a humidified 5% $CO_2$ incubator for 3-4 weeks. To terminate the test: cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is total lysing of the cell monolayer.

96 Well Plate Assay

The 96 well plate assay was performed similarly to the plaque assay above with modifications. SCP cells were seeded at $1 \times 10^4$ cells per well in 0.1 ml DME medium. When confluent, the wells were washed with serum free MEM and 25 ul of virus added in M-199 supplemented with 2% lamb serum. After 1 hour, 75 uL of medium containing test compound was added to each well containing virus. After 2-3 weeks incubation the cytopathic effect of the virus was determined by staining with a vital stain. Cell viability was measured by determining stain density using a 96 well plate reader.

Control wells without virus were completed to determine the toxicity of compounds.

RESULTS

Table 1, below, sets forth the results of the assay for representative compounds of Examples herein compared to the N-butyl derivative of 1,5-dideoxy-1,5-imino-D-glucitol (N-Bu-DNJ) as a control standard.

TABLE 1

| PLAQUE REDUCTION ASSAY | | | |
|---|---|---|---|
| Compound Example No. | Concentration (mM) | Toxicity | Antiviral Activity |
| 3 | 1.0 | 0 | A |
|  | 0.5 | 0 | A |
| 4 | 1.0 | 0 | A |
|  | 0.5 | 0 | A |
| 5 | 1.0 | 0 | A |
|  | 0.5 | 0 | A |
|  | 0.1 | 0 | A |
| 7 | 1.0 | 0 | A |
|  | 0.5 | 0 | A |
|  | 0.1 | 0 | A |
| N-Bu-DNJ | 1.0 | 2 | A |
|  | 0.1 | 1 | A |
|  | 0.01 | 0 | I |
|  | 0.001 | 0 | I |
| 8 | 1.0 | 0 | A |
|  | 0.1 | 0 | A |
| 10 | 0.125 | 3 | A |
|  | 0.0625 | 2 | A |
|  | 0.03125 | 1 | A |
| 12 | 0.03125 | 2 | A |
|  | 0.0156 | 1 | A |
|  | 0.0075 | 1 | A |
| 14 | 1.0 | 4 | Toxic |
|  | 0.1 | 2 | A |
|  | 0.01 | 0 | A |
|  | 0.001 | 0 | A |
| 16 | 1.0 | 4 | Toxic |
|  | 0.1 | 1 | A |
|  | 0.01 | 0 | A |
|  | 0.001 | 0 | A |
| 17 | 0.1 | 4 | Toxic |
|  | 0.01 | 2 | A |
| 18 | 1.0 | 0 | A |
|  | 0.1 | 1 | A |
| 20 | 1.0 | 2 | A |
|  | 0.1 | 1 | A |
|  | 0.01 | 0 | A |

TABLE 1-continued

PLAQUE REDUCTION ASSAY

| Compound Example No. | Concentration (mM) | Toxicity | Antiviral Activity |
|---|---|---|---|
| 22 | 1.0 | 0 | A |
|  | 0.1 | 0 | A |
|  | 0.01 | 0 | A |
| 24 | 2.0 | 0 | A |
| 25 | 1.0 | 2 | A |
|  | 0.1 | 1 | A |

A = active compound
I = inactive compound
Toxicity graded on 0 to 4 scale 0 = no toxicity, 4 = total cell lysates
N-Bu-DNJ = N-butyl-deoxynojirimycin used as a control standard.

Table 2, below, sets forth additional results of the foregoing assay in which the antiviral activity is stated in terms of % plaque reduction.

TABLE 2

PLAQUE REDUCTION ASSAY

| Compound Example No. | Concentration (mM) | Toxicity | Antiviral Activity |
|---|---|---|---|
| 27 | 1.0 | 3 | 65 |
|  | 0.1 | 0 | 12 |
| 28 | 1.0 | 4 | 87 |
|  | 0.1 | 2 | 44 |
| 33 | 1.0 | 3 | 63 |
|  | 0.1 | 0 | 28 |
|  | 0.01 | 0 | 21 |
| 35 | 1.0 | 3 | 94 |
|  | 0.1 | 1 | 90 |
|  | 0.01 | 0 | 10 |
| 36 | 1.0 | 4 | Toxic |
|  | 0.1 | 4 | Toxic |
|  | 0.01 | 0 | 76 |
|  | 0.001 | 0 | 4 |
| 38 | 1.0 | 4 | Toxic |
|  | 0.1 | 2 | 80 |
|  | 0.01 | 0 | 54 |
|  | 0.001 | 0 | 47 |
| 39 | 1.0 | 3 | 95 |
|  | 0.1 | 1 | 56 |
|  | 0.01 | 0 | 19 |
| 40 | 1.0 | 4 | — |
|  | 0.1 | 3 | — |
|  | 0.01 | 1 | 46 |
|  | 0.001 | 0 | 29 |
| 42 | 1.0 | 4 | Toxic |
|  | 0.1 | 2 | 97 |
|  | 0.01 | 1 | 13 |
|  | 0.001 | 0 | 31 |
| 47 | 1.0 | 4 | Toxic |
|  | 0.1 | 1 | 86 |
|  | 0.01 | 0 | 64 |
|  | 0.001 | 0 | 9 |
| 49 | 1.0 | 0 | 98 |
| 50A | 1.0 | 4 | Toxic |
|  | 0.1 | 1 | 49 |
|  | 0.01 | 0 | 20 |
| 50B | 1.0 | 2 | 76 |
|  | 0.1 | 1 | 75 |
|  | 0.01 | 0 | 33 |
|  | 0.001 | 0 | 17 |
| 51 | 1.0 | 4 | Toxic |
|  | 0.1 | 1 | 91 |
|  | 0.01 | 0 | 57 |
|  | 0.001 | 0 | 12 |
| 52 | 1.0 | 4 | Toxic |
|  | 0.1 | 0 | 98 |
|  | 0.01 | 0 | 37 |
|  | 0.001 | 0 | 16 |
| 53 | 1.0 | 4 | Toxic |
|  | 0.1 | 2 | 100 |
|  | 0.01 | 0 | 81 |
|  | 0.001 | 0 | 28 |
| 55 | 1.0 | 4 | Toxic |
|  | 0.1 | 0 | 95 |
|  | 0.01 | 0 | 37 |
|  | 0.001 | 0 | 11 |

TABLE 2-continued

PLAQUE REDUCTION ASSAY

| Compound Example No. | Concentration (mM) | Toxicity | Antiviral Activity |
|---|---|---|---|
| 56 | 1.0 | 0 | 56 |
|  | 0.1 | 0 | 16 |
|  | 0.01 | 0 | 13 |
| 62 | 1.0 | 2 | 97 |
|  | 0.1 | 1 | 91 |
|  | 0.01 | 0 | 49 |
| 63 | 1.0 | 2 | 90 |
|  | 0.1 | 0 | 2 |
| 66 | 1.0 | 2 | 100 |
|  | 0.1 | 1 | 88 |
|  | 0.01 | 0 | 38 |
|  | 0.001 | 0 | −3 |

EXAMPLE 44

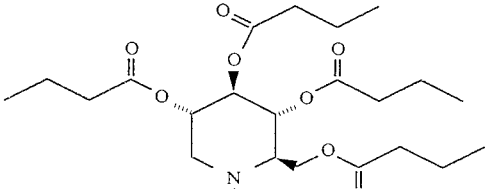

1,5-(Butylimino)-1,5-dideoxy-D-glucitol, tetrabutyrate.

A solution of 1,5-dideoxy-1,5-imino-D-glucitol, tetrabutyrate (0.43 g, 0.001 mole), butyraldehyde (0.2 g, 0.0028 mole) and 4% Palladium black in 25 ml methanol was hydrogenated (5 psi/25° C./71 hrs). After filtering the resulting mixture, the filtrate was concentrated in vacuo. The product was purified by silica gel chromatography and crystallized from cold pentane (DSC-38.93° C.). The structure assignment was supported by NMR, infrared spectra and elemental analysis.

Analysis calcd. for $C_{22}H_{45}NO_8$: C, 62.50; H, 9.08; N, 2.80. Found: C, 62.80; H, 9.24; N, 2.75.

EXAMPLE 45

4,4,4-Trifluorobutanoyl chloride

Ethyl 4,4,4-trifluorobutyrate (20.0 g, 0.118 mole) was added to water (150 ml) containing sodium hydroxide (9.4 g, 0.235 mole). The reaction was warmed to reflux for 2 hrs, cooled to room temperature at which time sulfuric acid was added to adjust to pH 2. The product acid was extracted into ethyl ether, dried over anhydrous sodium sulfate and filtered. The product acid was isolated by vacuum distillation (85°–92° C./15 mm).

4,4,4-Trifluorobutyric acid (5.8 g, 0.041 mole) was dissolved in benzene (30 ml). Oxalyl chloride (6.2 g, 0.049 mole) was added and the reaction stirred for 20 hrs. The benzene and excess oxalyl chloride was removed by distillation to give the title compound.

EXAMPLE 46

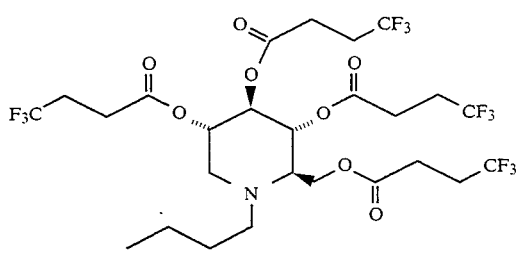

1,5-(Butylimino)-1,5-dideoxy-D-glucitol, tetra(4,4,4-trifluorobutanoate)

A solution of the product of Example 45 (0.041 mole) in tetrahydrofuran (10 ml) was added to a solution of 1,5-(butylimino)-1,5-dideoxy-D-glucitol (1.5 g, 0.0068 mole) in pyridine (50 ml) and stirred for 20 hrs at room temperature. The reaction was heated to 50° C. for 2 hrs and stirred at room temperature for 20 hrs. Water (10 ml) was added and the reaction was concentrated to an oily solid. Water (50 ml) was added and the product was extracted into ethyl acetate (75 ml). The ethyl acetate was washed with water (50 ml), dried over anhydrous sodium sulfate, filtered and concentrated to an oil. The product was purified by silica gel chromatography and the structure was verified by NMR.

EXAMPLE 47

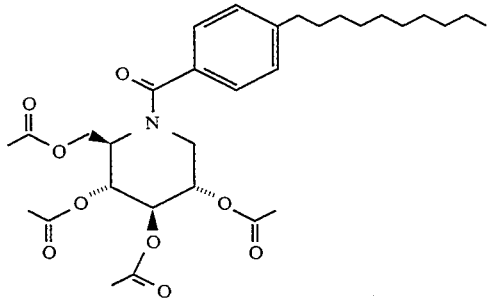

Triethylamine (0.2 ml) was added to a solution of 1,5-dideoxy-1,5-imino-D-glucitol, tetracetate (0.25 g, 0.00075 mole) and p-decylbenzoyl chloride (0.23 g, 0.00083 mole) in tetrahydrofuran (25 ml) and stirred for 20 hrs at room temperature. The white solid was removed by filtration and the filtrate was concentrated to an oil. The product was purified by silica gel chromatography. The structure assignment was supported by NMR, infrared spectra and elemental analysis (575.71).

Analysis calcd. for $C_{31}H_{45}NO_9 \cdot \frac{1}{2} H_2O$: C, 63.68; H, 7.93; N, 2.40. Found: C, 63.86; H, 7.86; N, 2.34.

EXAMPLE 48

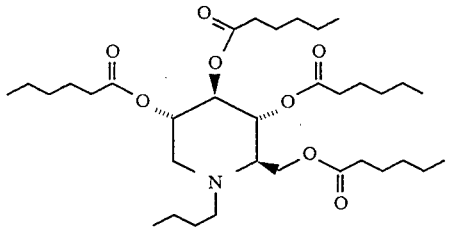

4-Dimethylamino pyridine (100 mg) was added to a solution of 1,5-(butylimino)-1.,5-dideoxy-D-glucitol (2.19 g, 0.01 mole) and hexanoic anhydride (12.8 g, 0.06 mole) in pyridine (50 ml) and the reaction was stirred at room temperature for 44 hrs. Water (50 ml) was added and the reaction was concentrated. Water (100 ml) was added and the product extracted into ethyl acetate (2×50 ml). The combined ethyl acetate extracts were dried over anhydrous sodium sulfate, filtered and concentrated. The product was purified by silica gel chromatography. The structure assignment was supported by NMR and elemental analysis (611.87).

Analysis calcd. for $C_{34}H_{61}NO_8 \cdot 0.4M\ H_2O$. C, 65.97; H, 10.06; N, 2.26. Found: C, 65.98; H, 9.91; N, 2.11.

EXAMPLE 49

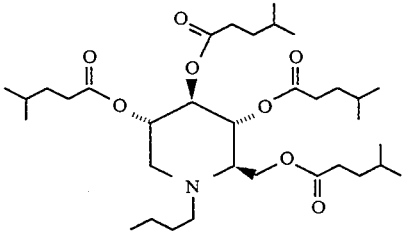

A solution of 4-methylvaleryl chloride (0.81 g, 0,006 mole) in tetrahydrofuran (5 ml) was added to a solution of 1,5-(butylimino)-1,5-dideoxy-D-glucitol (0.22 g, 0,001 mole) in pyridine (15 ml) and stirred at room temperature for 4 days. Water (5 ml) was added and the reaction was concentrated to an oily solid. Water (25 ml) and ethyl acetate (50 ml) was added and the layers were separated. The ethyl acetate was washed with water (25 ml), dried over anhydrous sodium sulfate, filtered and concentrated to an oil. The product was purified by silica gel chromatography. The structure assignment was supported by NMR, infrared spectra and elemental analysis (611.87).

Analysis calcd. for $C_{34}H_{61}NO_8$: C, 66.74; H, 10.05; N, 2.29. Found: C, 66.72; H, 10.25; N, 2.29.

EXAMPLE 50A

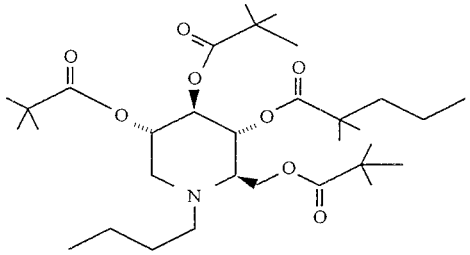

The title compound was prepared by the method of Example 48 by substituting trimethylacetic anhydride for hexanoic anhydride. The structure was supported by NMR.

EXAMPLE 50B

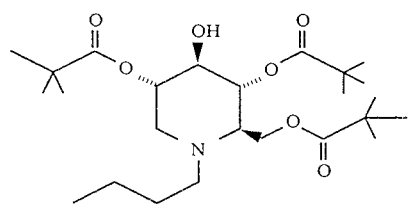

The title compound was isolated from Example 50A. The structure was supported by NMR.

EXAMPLE 51

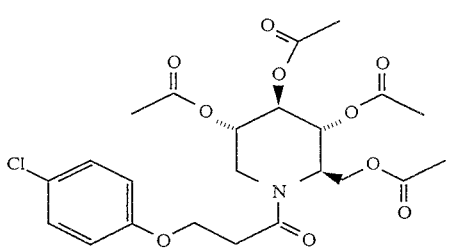

The title compound was prepared by the method of Example 47 by substituting the acid chloride [prepared from 3-(p-chlorophenoxy)propionic acid by the method of Example 45 ]for p-decyl benzoyl chloride. The structure was supported by NMR, infrared spectroscopy and elemental analysis (513.93).

Analysis calcd. for $C_{23}H_{28}NO_{10}Cl$: C, 53.75; H, 5.49; N, 2.73. Found: C, 53.82; H, 5.70; N, 2.66.

EXAMPLE 52

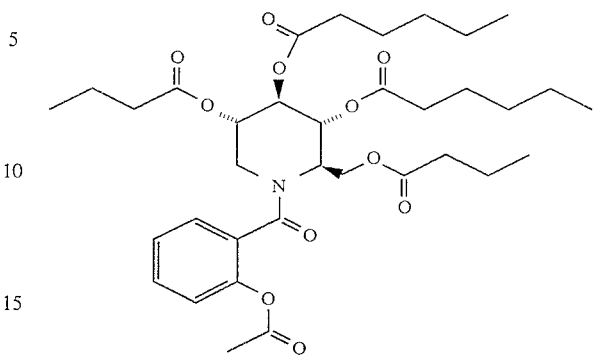

The title compound was prepared by the method of Example 47 by substituting 1,5-dideoxy-1,5-imino-D-glucitol, tetrabutyrate for the corresponding tetraacetate and by substituting acetylsalicyloxy chloride for p-decylbenzoyl chloride. The structure was supported by NMR, infrared spectroscopy and elemental analysis (605.69).

Analysis calcd. for $C_{31}H_{43}NO_{11}$: C, 61.47; H, 7.16; N, 2.31. Found: C, 61.31; H, 7.16; N, 2.30.

EXAMPLE 53

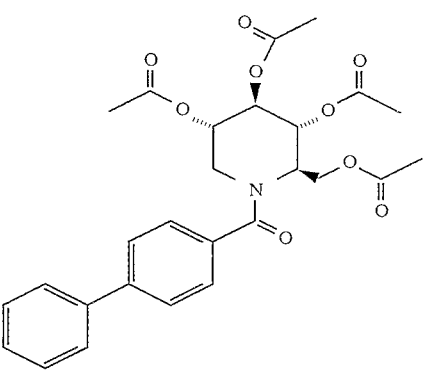

The title compound was prepared by the method of Example 47 by substituting 4-biphenylcarbonyl chloride for p-decyl benzoyl chloride. The structure was supported by NMR, infrared spectroscopy and elemental analysis (511.53).

Analysis calcd. for $C_{27}H_{29}NO_9$: C, 63.40; H, 5.71; N, 2.74. Found: C, 63.38; H, 5.70; N, 2.77.

EXAMPLE 54

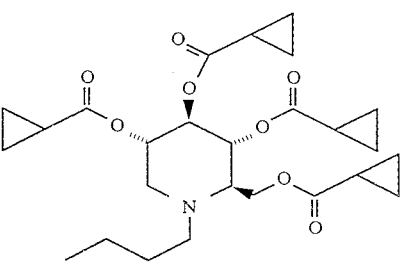

The title compound was prepared by the method of Example 49 by substituting cyclopropanecarbonyl chloride for 4-methylvaleryl chloride. The structure was supported by NMR, infrared spectroscopy and elemental analysis (491.59). DSC 90.47° C.

Analysis calcd. for $C_{26}H_{37}NO_8 \cdot 0.5$ M $H_2O$: C, 62.38; H, 7.65; N, 2.80. Found: C, 62.46; H, 7.35; N, 2.79.

EXAMPLE 55

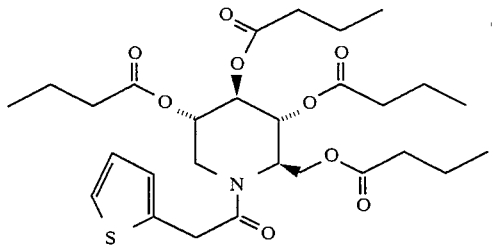

The title compound was prepared by the method of Example 47 by substituting 1,5-dideoxy-1,5-imino-D-glucitol, tetrabutyrate for the corresponding tetraacetate and by substituting 2-thiopheneacetyl chloride for p-decyl benzoyl chloride. The structure was supported by NMR and elemental analysis (567.70).

Analysis calcd. for $C_{28}H_{41}NO_9S$: C, 59.24; H, 7.28; N, 2.47. Found: C, 59.06; H, 7.11; N, 2.50.

EXAMPLE 56

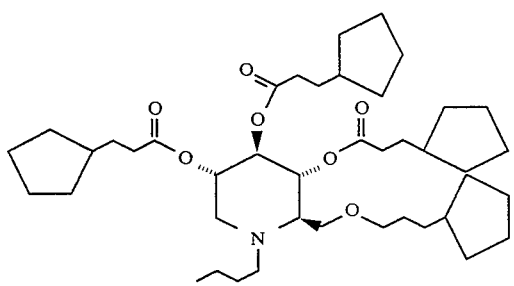

The title compound was prepared by the method of Example 49 by substituting 3-cyclopentylpropionyl chloride for 4-methylvalerylcarbonyl chloride. The structure was suppored by NMR, infrared spectroscopy and elemental analysis (716.02).

Analysis calcd. for $C_{42}H_{69}NO_8$: C, 70.45; H, 9.71; N, 1.96. Found: C, 70.72; H, 9.68; N, 1.97.

EXAMPLE 57

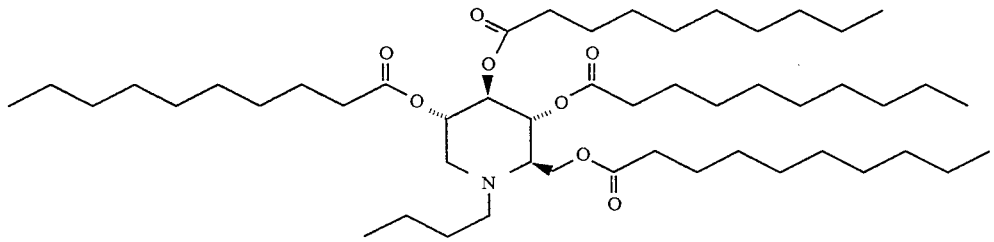

The title compound was prepared by the method of Example 48 by substituting decanoic anhydride for hexanoic anhydride. The structure was supported by, NMR, infrared spectroscopy and elemental analysis (836.30).

Analysis calcd. for $C_{50}H_{93}NO_8$: C, 71.81; H, 11.21; N, 1.67. Found: C, 71.64; H, 11.46; N, 1.37.

EXAMPLE 58

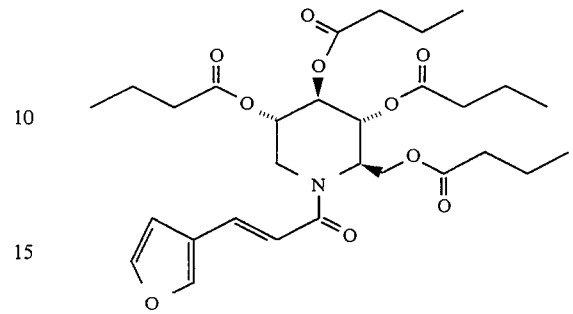

The title compound was prepared by the method of Example 47 by the substitution of trans-3-furanacrylic acid chloride (from trans-3-furanacrylic acid and oxalyl chloride) for p-decyl benzoyl chloride and the product of Example 42 for the product of Example 3. The structure was supported by NMR and elemental analysis (563.65).

Analysis calcd. for $C_{29}H_{41}NO_{10} \cdot \frac{3}{4}$M $H_2O$: C, 60.35; H, 7.42; N, 2.43. Found: C, 60.44; H, 7.66; N, 2.53.

EXAMPLE 59

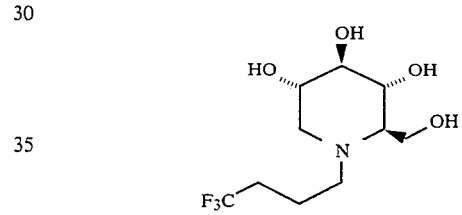

A solution of 1,5-dideoxy-1,5-imino-D-glucitol (6.07 g, 0.0372 mole), 4,4,4-trifluoro-1-bromobutane (7.1 g, 0.0372 mole) and potassium carbonate (2.57 g, 0.0186 mole) was stirred in dimethylformamide (400 ml) for 37 days. The reaction was filtered and concentrated to an oil. The product was purified by silica gel chromatography and crystallized from ethyl acetate. The structure of the title compound was supported by NMR and elemental analysis (273.25).

Analysis calcd. for $C_{10}H_{18}NO_4F_3$: C, 43.96; H, 6.64; N, 5.13. Found: C, 43.89; H, 6.69; N, 4.73.

EXAMPLE 60

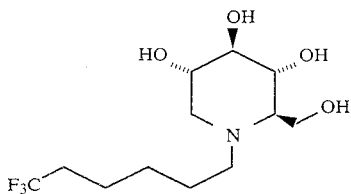

A solution of 1,5-dideoxy-1,5-imino-D-glucitol (5.22 g, 0,032 mole), 6,6,6-trifluoro-1-bromohexane (7.0 g, 0,032 mole) and silver oxide (3.96 g, 0.032 mole) was stirred in dimethyl formamide (45 ml) and water (45 ml) for 48 hrs at room temperature and then heated to between 62°–74° C. for 6 days. The solution was filtered and concentrated to an oily solid. The product was purified by silica gel chromatography and converted to the hydrochloride salt with HCl. The salt was passed through Amberlite IRA-400 (OH) ion exchange resin with water and stripped. The concentrate was purified by silica gel chromatography. The structure of the title compound was supported by NMR and elemental analysis.

Analysis calcd. for $C_{12}H_{22}NO_4F_3 \cdot \frac{1}{4} H_2O$: C, 47.13; H, 7.42; N, 4.58. Found: C, 46.96; H, 7.32; N, 4.58.

EXAMPLE 61

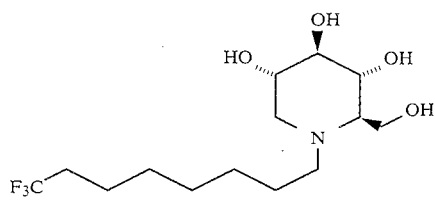

The title compound was prepared by the method of Example 60 by substituting 8,8,8-trifluoro-1-bromooctane for 6,6,6-trifluoro-l-bromohexane. The structure was supported by NMR, infrared spectroscopy and elemental analysis.

Analysis calcd. for $C_{14}H_{26}NO_4F_3 \cdot \frac{1}{4} H_2O$: C, 50.37; H, 8.00; N, 4.20. Found: C, 50.32; H, 8.10; N, 4.19.

EXAMPLE 62

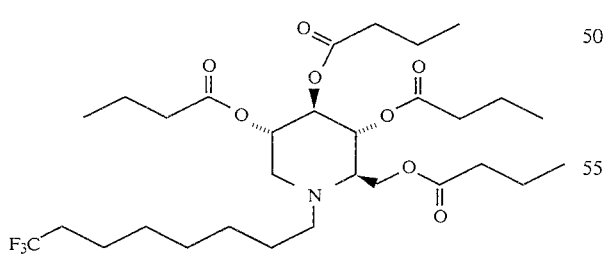

1,5-(8,878-Trifluorooctylimino)-1,5-dideoxy-D-glucitol (0.30 g, 0.00091 mole) and butyric anhydride (0.86 g, 0.00546 mole) were stirred in pyridine (10 ml) for 18 days at room temperature. Water (25 ml) was added to the solution, stirred for 1 hr and concentrated to an oil. Methyl alcohol (50 ml) was added and the solution concentrated to an oil. Ethyl acetate (10 ml) was added, the solution was filtered and the filtrate concentrated to an oil. The product was purified by silica gel chromatography. The structure of the title compound was supported by NMR, infrared spectroscopy and elemental analysis (609.73).

Analysis calcd. for $C_{30}H_{50}NO_8F_3$: C, 59.10; H, 8.27; N, 2.30. Found: C, 59.06; H, 8.31; N, 2.22.

EXAMPLE 63

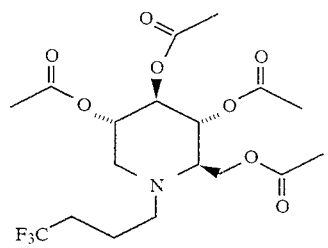

The title compound was prepared by the method of Example 62 by substituting the product of Example 59 for the product of Example 61 and acetic anhydride for butyric anhydride. The structure was supported by NMR, infrared spectroscopy and elemental analysis (441.4).

Analysis calcd. for $C_{18}H_{26}NO_8F_3$: C, 48.98; H, 5.94; N, 3.17. Found: C, 48.73; H, 5.92; N, 3.08.

EXAMPLE 64

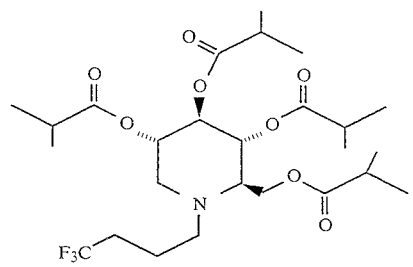

The title compound was prepared by the method of Example 63 by substituting isobutyric anhydride for acetic anhydride. The structure was supported by NMR, infrared spectroscopy and elemental analysis (553.6).

Analysis calcd. for $C_{26}H_{42}NO_8F_3$: C, 56.41; H, 7.65; N, 2.53. Found: C, 56.26; H, 7.61; N, 2.48.

EXAMPLE 65

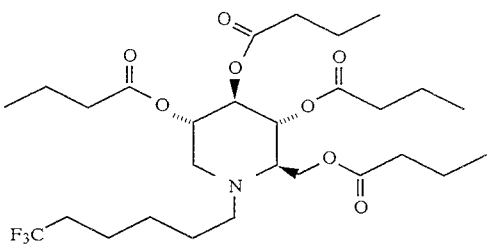

The title compound was prepared by the method of Example 62 by substituting the product of Example 60 for the product of Example 61. The structure was supported by NMR, infrared spectroscopy and elemental analysis (581.7).

Analysis calcd. for $C_{28}H_{46}NO_8F_3$: C, 57.82; H, 7.97; N, 2.41. Found: C, 57.86; H, 8.19; N, 2.39.

EXAMPLE 66

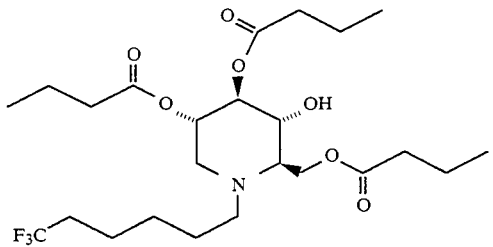

The title compound was isolated from the reaction of Example 65. The structure was supported by NMR.

EXAMPLE 67

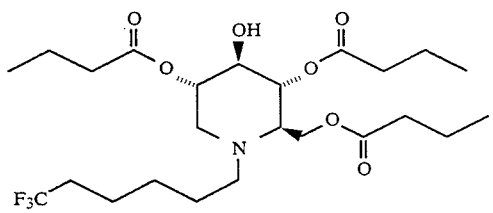

The title compound was isolated from the reaction of Example 65. The structure was supported by NMR.

EXAMPLE 68

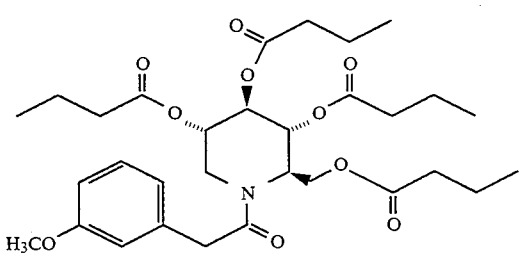

The title compound was prepared by the method of Example 58 by the substitution of 3-methoxyphenylacetyl chloride for trans-3-furanacrylic acid chloride. The structure was supported by NMR.

EXAMPLE 69

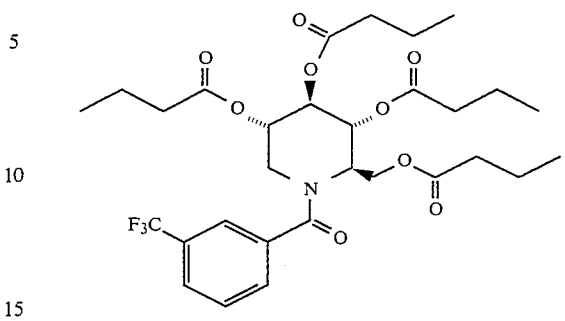

The title compound was prepared by the method of Example 58 by the substitution of 3-(trifluoromethyl)-benzoyl chloride for trans-3-furanacrylic acid chloride. The structure was supported by NMR and elemental analysis (615.65).

Analysis calcd. for $C_{30}H_{40}NO_9F_3$: C, 58.53; H, 6.55; N, 2.28. Found: C, 58.32; H, 6.57; N, 2.18.

Still other novel compounds of the invention can be made by methods analogous to the methods employed in the foregoing examples. Thus, branched chain analogs can be made by the method used in Example 47 to prepare, e.g., 1,5-[[2-(4-chlorophenoxy)-2-methyl-1-oxopropyl]imino]-1,5-dideoxy-D-glucitol, tetraacetate. The method of Example 49 can be used to similarly prepare 1,5-(butylimino)-1,5-dideoxy-D-glucitol, tetra(3-methoxy-3-oxopropanoate). Likewise, unsaturated radicals can be introduced into the compounds in place of the corresponding saturated radicals to prepare analogous unsaturated compounds such as, e.g., 1,5-(butylimino)-1,5-dideoxy-D-glucitol, tetra(3E-hexanoate) and 1,5-(butylimino)-1,5-dideoxy-D-glucitol, tetra(2-propenoate). Aromatic substituted radicals can be introduced into the O-acylated groups to prepare compounds such as, e.g., 1,5-(butylimino)-1,5-dideoxy-D-glucitol, tetra[3-(4'-methoxyphenyl)]propanoate. So also other substituted aromatic radicals can be used for the N-aroyl groups to prepare compounds such as, e.g., 1,5-dideoxy-1,5-[[2-(4-fluorophenoxy)-1-oxoethyl-]imino]-D-glucitol, tetraacetate. Still other compounds within the scope of the invention will be apparent to the person skilled in the art after reading the present disclosure.

The following illustrative reaction schemes can be used for preparing the novel antiviral compounds of the invention from the amine, 1,5-dideoxy-1,5-imino-D-glucitol, in which R, $R_1$ and $R_2$ are suitable radicals as defined hereinbefore.

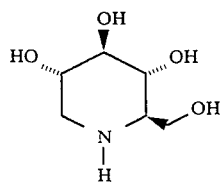

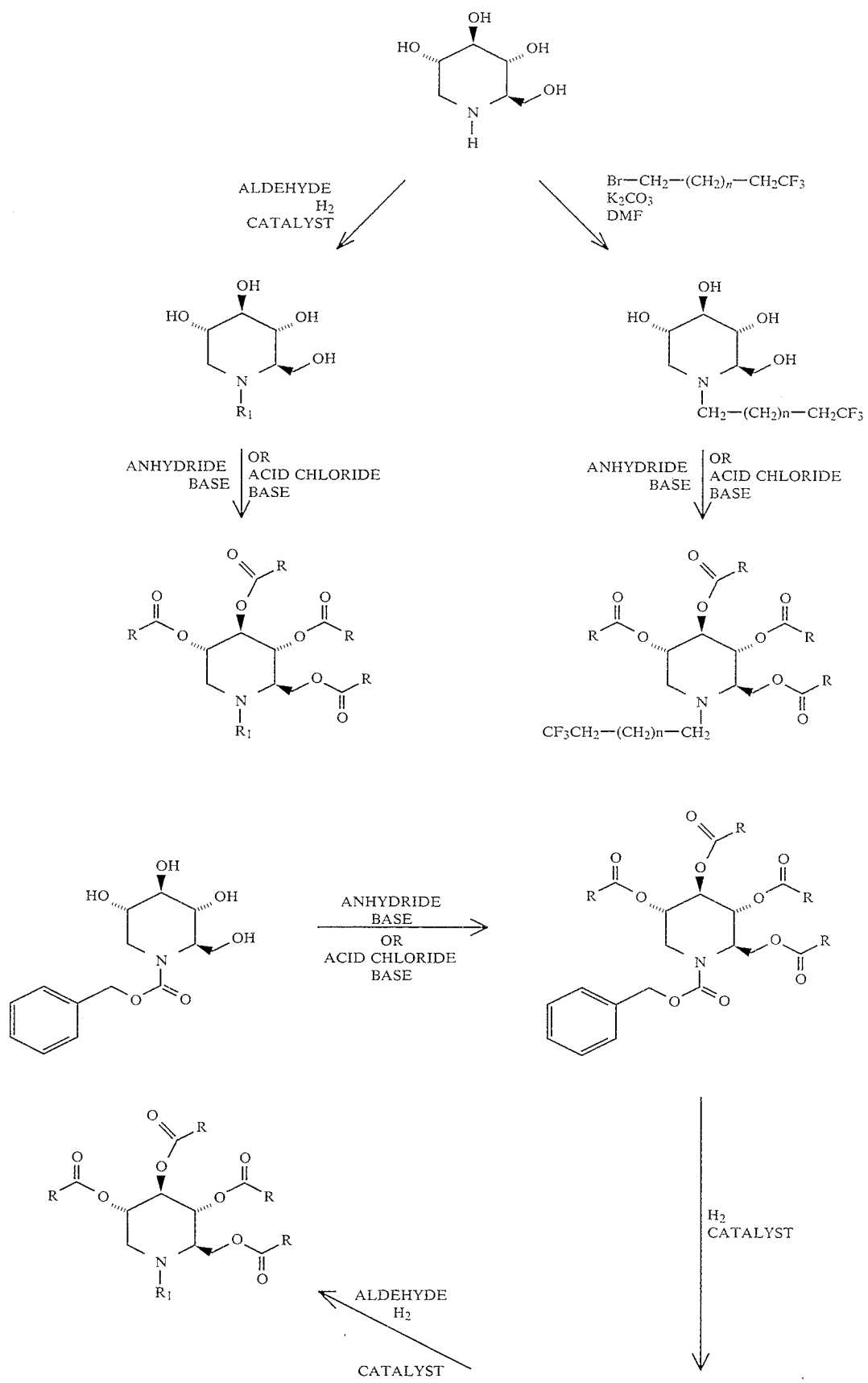

-continued

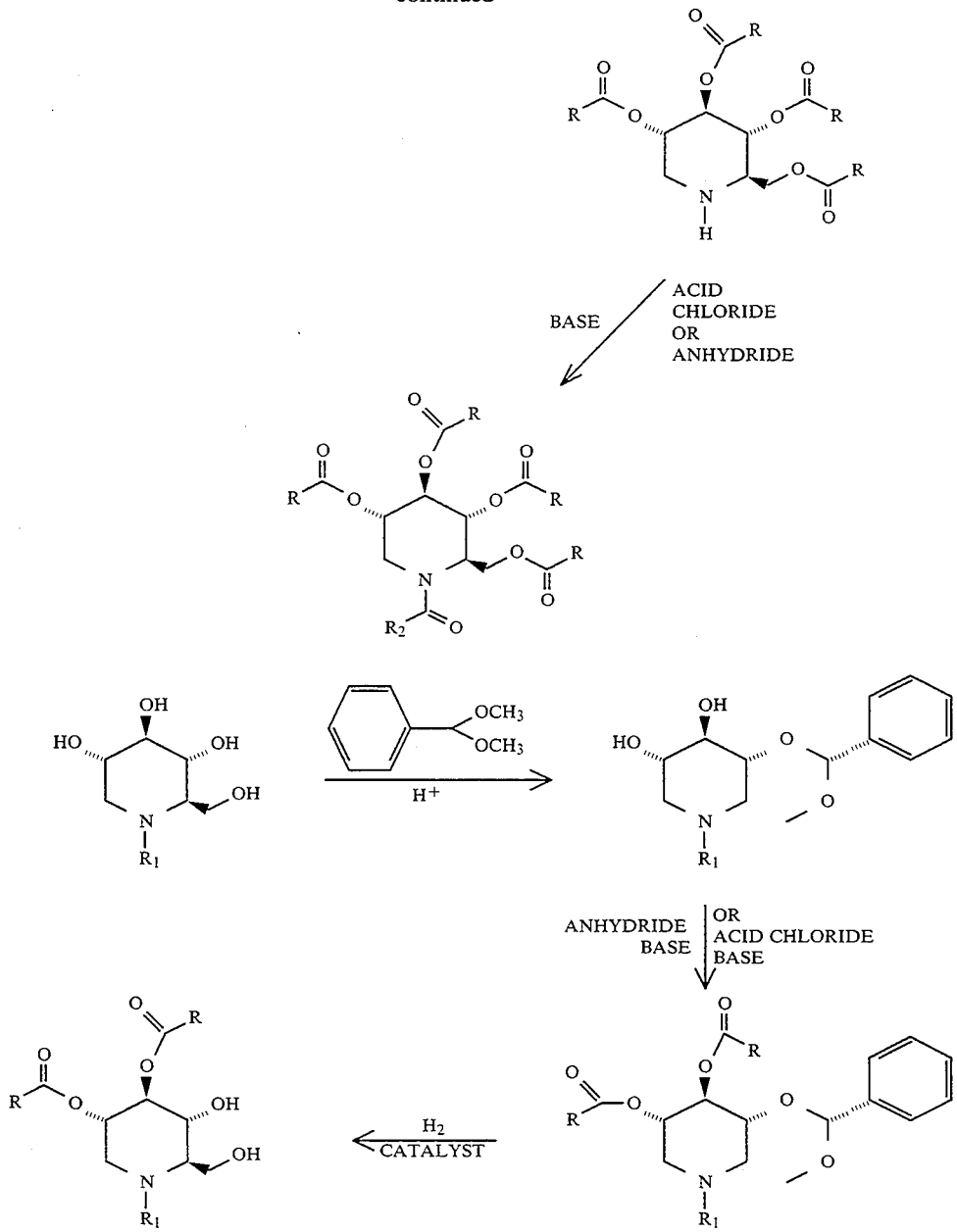

EXAMPLE 70

In pharmacokinetic and metabolism studies in the Rhesus monkey and rat, an illustrative antiviral compound 16 of the invention, namely 1,5-(butylimino)-1,5-dideoxy-D-glucitol tetrabutyrate, has been demonstrated upon metabolic transformation in vivo to provide controlled, sustained levels of a metabolite which is the antiviral compound 1,5-(butylimino)-1,5-dideoxy-D-glucitol. The parent tetrabutyrate compound consequently serves as an antivirally effective and useful pro-drug of the latter compound to which it is metabolized in the gut. Thus, oral administration of [$^{14}$C]SC-pro-drug to either species yielded only [$^{14}$C]SC-metabolite compound in the plasma. The parent pro-drug was not detected. The metabolic profiles of either radiolabeled compounds in the monkey were determined to be the same in plasma and urine when the compounds were administered by the oral route. The oral bioactivity of the metabolite compound, measured as [$^{14}$C]-metabolite compound, was determined to be between 28% and 50% in the Rhesus monkey, depending on the vehicle used (e.g., 0.5% methyl cellulose and 0.1% polysorbate in water). It was approximately 82% in the rat with no parent pro-drug detected in the portal plasma. The blood levels of the metabolite compound, measured as part of a long term SIV infected monkey efficacy study, following oral dosing (high dose 750 mg/kg, low dose 250 mg/kg, administered every eight hours) with the pro-drug, yielded mean trough (cmin) plasma blood levels of the metabolite compound at eight hours post dosing of approximately 10 μg/mL and 6.8 μg/mL for the high and low doses, respectively. These data corroborate the pharmacokinetic data obtained in normal, uninfected monkeys in which the pro-drug does not significantly inhibit sucrase locally in the gut and thereby provides negative diarrheagenic results.

The antiviral agents described herein can be used for administration to a mammalian host infected with a lentivirus, e.g. visna virus or the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one milligram of the active compound and generally in the range to about 100 to 1000 mg/kg administered three times per day. Doses in the range of 250–750 mg/kg administered every eight hours to the Rhesus monkey provided effective plasma blood levels of the antiviral metabolite of active compound. The preferable route of administration is orally in the form of capsules, tablets, syrups, elixirs and the like, although parenteral administration also can be used. Suitable formulations of the active compound in pharmaceutically acceptable diluents and carriers in therapeutic dosage form can be prepared by reference to general texts in the field such as, for example, *Remington's Pharmaceutical Sciences*, Ed. Arthur Osol, 16th ed., 1980, Mack Publishing Co., Easton, Penna.

Various other examples will be apparent to the person skilled in the art after reading the present disclosure without departing from the spirit and scope of the invention. It is intended that all such other examples be included with the scope of the appended claims.

What is claimed is:

1. The method of inhibiting lentivirus by orally administering to a mammalian host susceptible to said lentivirus a virally inhibitory effective amount of an O-acylated derivative of an N-alkyl-1,5-dideoxy-1,5-imino-D-glucitol in which the N-alkyl is an $\omega,\omega,\omega$-trifluoralkyl group having from three to eight carbon atoms and the O-acylated groups are butyroyl.

2. The method of claim 1 in which the $\omega,\omega,\omega$-trifluoroalkyl group is 6,6,6-trifluorohexyl and the free hydroxyl groups at C2, C3 and C6 are O-acylated with butyroyl.

3. The method of claim 1, in which the $\omega,\omega,\omega$-trifluoroalkyl is 8,8,8-trifluorooctyl and all the free hydroxyl groups are O-acylated with butyroyl.

* * * * *